United States Patent
Zhou et al.

(10) Patent No.: US 9,689,032 B2
(45) Date of Patent: *Jun. 27, 2017

(54) METHODS AND SYSTEMS FOR SEQUENCING LONG NUCLEIC ACIDS

(71) Applicant: Centrillion Technology Holdings Corporation, Grand Cayman (KY)

(72) Inventors: Wei Zhou, Saratoga, CA (US); Rui Mei, Santa Clara, CA (US); Filip Crnogorac, Palo Alto, CA (US); Guochun Liao, Belmont, CA (US); Julian Lucas, Davis, CA (US)

(73) Assignee: Centrillion Technology Holdings Corporation (KY)

( * ) Notice: Subject to any disclaimer, the term of this patent is extended or adjusted under 35 U.S.C. 154(b) by 0 days.

This patent is subject to a terminal disclaimer.

(21) Appl. No.: 13/970,321

(22) Filed: Aug. 19, 2013

(65) Prior Publication Data
US 2014/0065604 A1 Mar. 6, 2014

Related U.S. Application Data

(63) Continuation of application No. 13/153,218, filed on Jun. 3, 2011, now abandoned.

(60) Provisional application No. 61/470,497, filed on Apr. 1, 2011, provisional application No. 61/477,173, filed on Apr. 20, 2011, provisional application No. 61/489,662, filed on May 24, 2011.

(51) Int. Cl.
*C12Q 1/68* (2006.01)

(52) U.S. Cl.
CPC ......... *C12Q 1/6869* (2013.01); *C12Q 1/6874* (2013.01)

(58) Field of Classification Search
USPC ............................................. 435/6.11; 506/7
See application file for complete search history.

(56) References Cited

U.S. PATENT DOCUMENTS

| | | | |
|---|---|---|---|
| 4,437,975 A | 3/1984 | Gillespie et al. | |
| 4,458,066 A | 7/1984 | Caruthers et al. | |
| 4,469,863 A | 9/1984 | Ts'o et al. | |
| 4,683,195 A | 7/1987 | Mullis et al. | |
| 4,683,202 A | 7/1987 | Mullis | |
| 4,883,750 A | 11/1989 | Whiteley et al. | |
| 4,988,617 A | 1/1991 | Landegren et al. | |
| 5,034,506 A | 7/1991 | Summerton et al. | |
| 5,143,854 A | 9/1992 | Pirrung et al. | |
| 5,216,141 A | 6/1993 | Benner | |
| 5,234,809 A | 8/1993 | Boom et al. | |
| 5,235,033 A | 8/1993 | Summerton et al. | |
| 5,242,794 A | 9/1993 | Whiteley et al. | |
| 5,386,023 A | 1/1995 | Sanghvi et al. | |
| 5,409,818 A | 4/1995 | Davey et al. | |
| 5,413,909 A | 5/1995 | Bassam et al. | |
| 5,470,705 A | 11/1995 | Grossman et al. | |
| 5,494,810 A | 2/1996 | Barany et al. | |
| 5,547,839 A | 8/1996 | Dower et al. | |
| 5,554,517 A | 9/1996 | Davey et al. | |
| 5,578,832 A | 11/1996 | Trulson et al. | |
| 5,602,240 A | 2/1997 | De Mesmaeker et al. | |
| 5,631,734 A | 5/1997 | Stern et al. | |
| 5,637,684 A | 6/1997 | Cook et al. | |
| 5,644,048 A | 7/1997 | Yau | |
| 5,705,628 A | 1/1998 | Hawkins | |
| 5,756,285 A * | 5/1998 | Fuller .......................... | 435/6.11 |
| 5,800,992 A | 9/1998 | Fodor et al. | |
| 5,834,758 A | 11/1998 | Trulson et al. | |
| 5,837,832 A | 11/1998 | Chee et al. | |
| 5,856,092 A | 1/1999 | Dale et al. | |
| 5,861,245 A | 1/1999 | Mcclelland et al. | |
| 5,871,928 A | 2/1999 | Fodor et al. | |
| 5,874,219 A | 2/1999 | Rava et al. | |
| 5,902,723 A | 5/1999 | Dower et al. | |
| 5,936,324 A | 8/1999 | Montagu | |
| 5,981,956 A | 11/1999 | Stern | |
| 6,025,601 A | 2/2000 | Trulson et al. | |
| 6,045,996 A | 4/2000 | Cronin et al. | |
| 6,063,603 A | 5/2000 | Davey et al. | |
| 6,090,555 A | 7/2000 | Fiekowsky et al. | |
| 6,141,096 A | 10/2000 | Stern et al. | |
| 6,185,030 B1 | 2/2001 | Overbeck | |
| 6,201,639 B1 | 3/2001 | Overbeck | |
| 6,214,246 B1 | 4/2001 | Craighead | |
| 6,218,803 B1 | 4/2001 | Montagu et al. | |
| 6,225,625 B1 | 5/2001 | Pirrung et al. | |
| 6,267,872 B1 | 7/2001 | Akeson et al. | |

(Continued)

FOREIGN PATENT DOCUMENTS

DE 10149786 A1 7/2003
DE 10214395 A1 10/2003

(Continued)

OTHER PUBLICATIONS

Ivashuta S, Uchiyama K, Gau M, Shimamoto Y. Linear amplification coupled with controlled extension as a means of probe amplification in a cDNA array and gene expression analysis during cold acclimation in alfalfa (*Medicago sativa* L.). J Exp Bot. Feb. 2002; 53(367):351-9.*
Ronaghi M. Pyrosequencing sheds light on DNA sequencing. Genome Res. Jan. 2001; 11(1):3-11. Review.*
U.S. Appl. No. 09/916,135, filed Jul. 25, 2001, Matsuzaki et al.
U.S. Appl. No. 14/009,089, filed Sep. 30, 2013, Zhou et al.
Adams, et al. The Genome Sequence of *Drosophila melanogaster*. Science. Mar. 24, 2000; 287 (5461): 2185-2195.
Bentley, et al. Accurate whole human genome sequencing using reversible terminator chemistry. Nature. Nov. 6, 2008;456(7218):53-9.
Constans, et al. Beyond Sanger: Toward the $1,000 Genome.The Scientist. Jun. 30, 2003; 17(13): 36.
Dempcy, et al. Synthesis of a thymidyl pentamer of deoxyribonucleic guanidine and binding studies with DNA homopolynucleotides. Proc Natl Acad Sci U S A. Jun. 20, 1995;92(13):6097-101.

(Continued)

*Primary Examiner* — Young J Kim
(74) *Attorney, Agent, or Firm* — Wilson Sonsini Goodrich & Rosati

(57) ABSTRACT

The present invention provides methods and systems for sequencing long nucleic acid fragments.

26 Claims, 7 Drawing Sheets

(56) References Cited

U.S. PATENT DOCUMENTS

| | | |
|---|---|---|
| 6,361,947 B1 | 3/2002 | Dong et al. |
| 6,386,749 B1 | 5/2002 | Watts et al. |
| 6,391,592 B1 | 5/2002 | Su et al. |
| 6,391,623 B1 | 5/2002 | Besemer et al. |
| 6,410,276 B1 | 6/2002 | Burg et al. |
| 6,440,662 B1 | 8/2002 | Gerwen et al. |
| 6,464,842 B1 | 10/2002 | Golovchenko et al. |
| 6,518,189 B1 | 2/2003 | Chou |
| 6,548,810 B2 | 4/2003 | Zaluzec et al. |
| 6,582,938 B1 | 6/2003 | Su et al. |
| 6,627,067 B1 | 9/2003 | Branton et al. |
| 6,632,611 B2 | 10/2003 | Su et al. |
| 6,673,615 B2 | 1/2004 | Denison et al. |
| 6,685,841 B2 | 2/2004 | Lopez et al. |
| 6,787,308 B2 | 9/2004 | Balasubramanian et al. |
| 6,833,246 B2 | 12/2004 | Balasubramanian |
| 6,852,487 B1 | 2/2005 | Barany et al. |
| 6,872,529 B2 | 3/2005 | Su et al. |
| 6,897,023 B2 | 5/2005 | Fu et al. |
| 6,958,225 B2 | 10/2005 | Dong et al. |
| 6,969,488 B2 | 11/2005 | Bridgham et al. |
| 7,001,724 B1 | 2/2006 | Greenfield et al. |
| 7,189,503 B2 | 3/2007 | Akeson et al. |
| 7,217,562 B2 | 5/2007 | Cao et al. |
| 7,238,485 B2 | 7/2007 | Akeson et al. |
| 7,258,838 B2 | 8/2007 | Li et al. |
| 7,267,966 B2 | 9/2007 | Dong et al. |
| 7,297,778 B2 | 11/2007 | Matsuzaki et al. |
| 7,300,788 B2 | 11/2007 | Matsuzaki et al. |
| 7,689,022 B2 | 3/2010 | Weiner et al. |
| 2002/0012930 A1 | 1/2002 | Rothberg et al. |
| 2003/0022207 A1 | 1/2003 | Balasubramanian et al. |
| 2003/0044781 A1 | 3/2003 | Korlach et al. |
| 2003/0058629 A1 | 3/2003 | Hirai et al. |
| 2003/0064376 A1 | 4/2003 | Makarov et al. |
| 2003/0064398 A1 | 4/2003 | Barnes |
| 2003/0100102 A1 | 5/2003 | Rothberg et al. |
| 2003/0148344 A1 | 8/2003 | Rothberg et al. |
| 2003/0186279 A1 | 10/2003 | Kennedy et al. |
| 2003/0186280 A1 | 10/2003 | Kennedy |
| 2004/0072217 A1 | 4/2004 | Kennedy |
| 2004/0106130 A1 | 6/2004 | Besemer et al. |
| 2004/0248144 A1 | 12/2004 | Mir |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0186576 A1 | 8/2005 | Chan et al. |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2006/0275782 A1 | 12/2006 | Gunderson et al. |
| 2007/0065816 A1 | 3/2007 | Dong et al. |
| 2007/0128649 A1 | 6/2007 | Young et al. |
| 2008/0102504 A1 | 5/2008 | Akeson et al. |
| 2008/0171316 A1 | 7/2008 | Golovchenko et al. |
| 2008/0248561 A1 | 10/2008 | Golovchenko et al. |
| 2009/0018024 A1 | 1/2009 | Church et al. |
| 2009/0088327 A1 | 4/2009 | Rigatti et al. |
| 2009/0203085 A1 | 8/2009 | Kurn et al. |
| 2009/0291475 A1 | 11/2009 | Lao et al. |
| 2010/0029498 A1 | 2/2010 | Gnirke et al. |
| 2010/0143900 A1 | 6/2010 | Peluso et al. |
| 2010/0297706 A1 | 11/2010 | Lee et al. |
| 2011/0009276 A1* | 1/2011 | Vermaas .............. C12Q 1/6874 506/7 |
| 2012/0083417 A1 | 4/2012 | Zhou et al. |
| 2012/0252682 A1 | 10/2012 | Zhou et al. |
| 2014/0315724 A1 | 10/2014 | Zhou et al. |

FOREIGN PATENT DOCUMENTS

| | | |
|---|---|---|
| DE | 10356837 A1 | 6/2005 |
| DE | 10 2004 009 704 A1 | 9/2005 |
| DE | 10 2004 025 744 A1 | 12/2005 |
| DE | 10 2004 025 745 A1 | 12/2005 |
| DE | 10 2004 025 746 A1 | 12/2005 |
| DE | 10 2004 025 694 A1 | 2/2006 |
| DE | 10 2004 025 695 A1 | 2/2006 |
| DE | 10 2004 025 696 A1 | 2/2006 |
| GB | 2398383 A | 8/2004 |
| WO | WO 88/10315 A1 | 12/1988 |
| WO | WO 90/06995 A1 | 6/1990 |
| WO | WO 96/40999 A1 | 12/1996 |
| WO | WO 99/47964 A1 | 9/1999 |
| WO | WO 01/32930 A1 | 5/2001 |
| WO | WO 02/29003 A2 | 4/2002 |
| WO | WO 02/088382 | 11/2002 |
| WO | WO 03/020968 | 3/2003 |
| WO | WO 03/031947 | 4/2003 |
| WO | WO 2005/044836 | 5/2005 |
| WO | WO 2008066245 A1 * | 6/2008 |
| WO | WO 2009/097626 A2 | 8/2009 |
| WO | WO 2010075188 A2 * | 7/2010 |
| WO | WO 2011/032040 A1 | 3/2011 |

OTHER PUBLICATIONS

Dong, et al. Flexible use of high-density oligonucleotide arrays for single-nucleotide polymorphism discovery and validation. Genome Res. Aug. 2011;11(8):1418-24.

European search report and written opinion dated Sep. 18, 2014 for European Patent Application No. 12762821.2.

Gao, et al. Oligonucleotide synthesis using solution photogenerated acids. J. Am. Chem. Soc. 1999; 120: 12698-12699.

Grossman, et al. High-density multiplex detection of nucleic acid sequences: oligonucleotide ligation assay and sequence-coded separation. Nucleic Acids Res. Oct. 25, 1994;22(21):4527-34.

Guo, et al. Four-color DNA sequencing with 3'-0-modified nucleotide reversible terminators and chemically cleavable fluorescent dideoxynucleotides. Proc Natl Acad Sci U S A. 2008. 105(27):9145-50. Epub Jun. 30, 2008.

International search report and written opinion dated Oct. 1, 2012 for PCT/US2012/000185.

Jenkins, et al. The Biosynthesis of Carbocyclic Nucleosides. Chem. Soc. Rev. 1995; 169-176.

Letsinger, et al. Effects of pendant groups at phosphorus on binding properties of d-ApA analogues. Nucleic Acids Res. Apr. 25, 1986;14(8):3487-99.

Levene, et al. Zero-mode waveguides for single-molecule analysis at high concentrations. Science. Jan. 31, 2003;299(5607):682-6.

Mag, et al. Synthesis and selective cleavage of an oligodeoxynucleotide containing a bridged internucleotide 5'-phosphorothioate linkage. Nucleic Acids Res. Apr. 11, 1991;19(7):1437-41.

Marguiles, et al. Genome sequencing in microfabricated high-density picolitre reactors. Nature. Sep. 15, 2005;437(7057):376-80. Epub Jul. 31, 2005.

Metzker, ML. Sequencing technologies—the next generation. Nat Rev Genet. 2010.11(1):31-46 Epub Dec. 8, 2009. Review.

Miller, et al. A simple salting out procedure for extracting DNA from human nucleated cells. Nucleic Acids Research. 1998: 16(3): 9-10.

Office action dated Feb. 19, 2013 for U.S. Appl. No. 13/153,218.

Rawls. Optimistic About Antisense: Promising clinical results and chemical strategies for further improvements delight antisense drug researchers. C & E News. Jun. 2, 1997; p. 35.

Saiki, et al . Enzymatic amplification of beta-globin genomic sequences and restriction site analysis for diagnosis of sickle cell anemia. Science. Dec. 20, 1985;230(4732):135-04.

Sprinzl, et al. Enzymatic incorporation of ATP and CTP analogues into the 3' end of tRNA. Eur J Biochem. Dec. 1977;81(3):579-89.

Venter, et al. Sequence of the Human Genome. Science. Feb. 16, 2001; 291(5507): 1304-1351.

(56) References Cited

OTHER PUBLICATIONS

Wu, et al. 3'-O-modified nucleotides as revers . . . [Proc Natl Acad Sci U S A. 2007]—PubMed—NCBI. Proc Natl Acad Sci U S A. Oct. 16, 2007;104(42):16462-7. Epub Oct. 8, 2007.
Yang, et al. Nucleoside alpha-thiotriphosphates, polymerases and the exonuclease III analysis of oligonucleotides containing phosphorothioate linkages. Nucleic Acids Res. 2007;35(9):3118-27. Epub Apr. 22, 2007.
Office action dated Feb. 13, 2015 for CN Application No. 201180056235.7 (with English translation).
U.S. Appl. No. 60/011,359, filed Feb. 9, 1996, Barany et al.
U.S. Appl. No. 60/364,731, filed Mar. 15, 2002, Weiner et al.
"Mammal," (Wikipedia.com; accessed Sep. 22, 2011.
"Virus," Wikipedia.com, accessed Apr. 18, 2012.
European search report and written opinion dated May 15, 2014 for EP Application No. 11827648.4.
How many species of bacteria are there? Wisegeek.com. Accessed Sep. 23, 2011.
International search report and written opinion dated Jan. 18, 2012 for PCT/US2011/053079.
Newton, et al. The production of PCR products with 5' single-stranded tails using primers that incorporate novel phosphoramidite intermediates. Nucleic Acids Res. Mar. 11, 1993;21(5):1155-62.
Office action dated Mar. 13, 2013 for U.S. Appl. No. 13/243,833.
Office action dated Jul. 27, 2012 for U.S. Appl. No. 13/243,833.
Schultz, et al. Single-target molecule detection with nonbleaching multicolor optical immunolabels. Proc Natl Acad Sci U S A. Feb. 1, 2000;97(3):996-1001.
Seo, et al. Four-color DNA sequencing by synthesis on a chip using photocleavable fluorescent nucleotides. Proc. Natl. Acad. Sci. USA. Apr. 26, 2005; 102(17):5926-5931.
European office action dated Aug. 12, 2015 for EP Application No. 11827648-4.
Office action dated Sep. 29, 2015 for CN Application No. 201180056235.7.
Co-pending U.S. Appl. No. 14/970,435, filed Dec. 15, 2015.
"Fish," (Wikipedia.com, accessed Nov. 2, 2014).
"Fungi," (Wikipedia.com; accessed Jun. 3, 2013).
"How many species of bacteria are there" (wisegeek.com; accessed Jan. 21, 2014).
"List of sequenced bacterial genomes" (Wikipedia.com; accessed Jan. 24, 2014).
"Murinae," (Wikipedia.com, accessed Mar. 18, 2013).
"Plant," (Wikipedia.com; accessed Mar. 8, 2013).
"Viruses" (Wikipedia.com, accessed Nov. 24, 2012).
Office action dated Jun. 29, 2015 for U.S. Appl. No. 13/243,833.
Office action dated Jun. 18, 2015 for CN Application No. 201280027272.X.

\* cited by examiner

FIG. 1

| Step | Length(bp) | Dark Base | |
|---|---|---|---|
| 1 | 7 | GCT | GGCTCTC |
| 2 | 14 | AGC | GGCTCTCAAGGGCA |
| 3 | 21 | TCG | GGCTCTCAAGGGCATCGGTCG |
| 4 | 25 | ACG | GGCTCTCAAGGGCATCGGTCGACGC |
| 5 | 35 | TCA | GGCTCTCAAGGGCATCGGTCGACGCTCTCCCTTAT |
| 6 | 40 | GCA | GGCTCTCAAGGGCATCGGTCGACGCTCTCCCTTATGCGAC |
| 7 | 46 | TCG | GGCTCTCAAGGGCATCGGTCGACGCTCTCCCTTATGCGACTCCTGC |
| 8 | 55 | ATG | GGCTCTCAAGGGCATCGGTCGACGCTCTCCCTTATGCGACTCCTGCATTAGGAAG |
| 9 | 63 | CAG | GGCTCTCAAGGGCATCGGTCGACGCTCTCCCTTATGCGACTCCTGCATTAGGAAGCAGCCCAG |
| 10 | 76 | ATG | GGCTCTCAAGGGCATCGGTCGACGCTCTCCCTTATGCGACTCCTGCATTAGGAAGCAGCCCAGTAGTAGGTTGAGG |
| 11 | 82 | GCT | GGCTCTCAAGGGCATCGGTCGACGCTCTCCCTTATGCGACTCCTGCATTAGGAAGCAGCCCAGTAGTAGGTTGAGGCCGTTG |
| 12 | 102 | AGC | GGCTCTCAAGGGCATCGGTCGACGCTCTCCCTTATGCGACTCCTGCATTAGGAAGCAGCCCAGTAGTAGGTTGAGGCCGTTGAGCACCGCCGCCGCAAGGAA |

FIG. 2

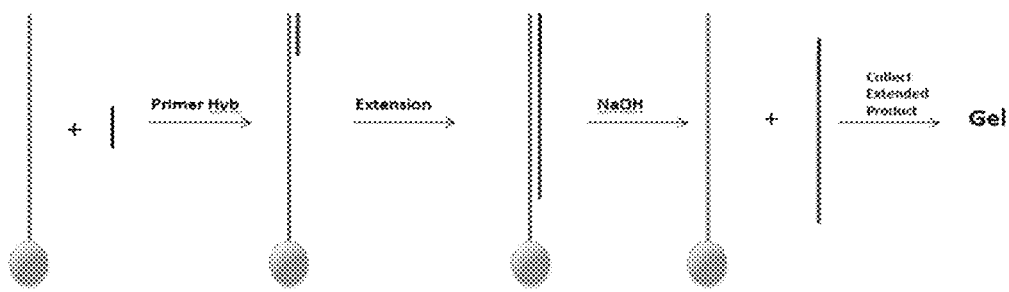

SEQUENCE LISTING

<160> NUMBER OF SEQ ID NOS: 11

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggctctcaag ggca                                                    14

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggctctcaag ggcatcggtc g                                            21

<210> SEQ ID NO 3
<211> LENGTH: 25

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggctctcaag ggcatcggtc gacgc                                            25

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggctctcaag ggcatcggtc gacgctctcc cttat                                 35

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggctctcaag ggcatcggtc gacgctctcc cttatgcgac                            40

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggctctcaag ggcatcggtc gacgctctcc cttatgcgac tcctgc                     46

<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggctctcaag ggcatcggtc gacgctctcc cttatgcgac tcctgcatta ggaag           55

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggctctcaag ggcatcggtc gacgctctcc cttatgcgac tcctgcatta ggaagcagcc      60
cag                                                                    63

<210> SEQ ID NO 9
```

```
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggctctcaag ggcatcggtc gacgctctcc cttatgcgac tcctgcatta ggaagcagcc    60
cagtagtagg ttgagg                                                    76

<210> SEQ ID NO 10
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggctctcaag ggcatcggtc gacgctctcc cttatgcgac tcctgcatta ggaagcagcc    60
cagtagtagg ttgaggccgt tg                                             82

<210> SEQ ID NO 11
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ggctctcaag ggcatcggtc gacgctctcc cttatgcgac tcctgcatta ggaagcagcc    60
cagtagtagg ttgaggccgt tgagcaccgc cgccgcaagg aa                      102
```

METHODS AND SYSTEMS FOR SEQUENCING LONG NUCLEIC ACIDS

CROSS-REFERENCE

This application is a continuation of U.S. application Ser. No. 13/153,218 filed Jun. 3, 2011, now abandoned, which claims the benefit of U.S. Provisional Application Nos. 61/470,497, filed Apr. 1, 2011; 61/477,173, filed Apr. 20, 2011; and 61/489,662, filed May 24, 2011, each of which is incorporated by reference in its entirety.

SEQUENCE LISTING

The instant application contains a Sequence Listing which has been submitted electronically in ASCII format and is hereby incorporated by reference in its entirety. Said ASCII copy, created on Oct. 15, 2013, is named 38558-705.301 SL.txt and is 3,350 bytes in size.

BACKGROUND

Nucleic acid sequencing is important for biological research, clinical diagnostics, personalized medicine and pharmaceutical development and many other fields. Cost effective and fast sequencing is needed for many applications, such as, but not limited to for microbial or pathogen detection and identification, and genetic identification for subjects. For example, applications can include, but not be limited to paternity testing and in forensic science (Reynolds et al., Anal. Chem., 63:2-15 (1991)), for organ-transplant donor-recipient matching (Buyse et al., Tissue Antigens, 41:1-14 (1993) and Gyllensten et al., PCR Meth. Appl, 1:91-98 (1991)), for genetic disease diagnosis, prognosis, and pre-natal counseling (Chamberlain et al., Nucleic Acids Res., 16:11141-11156 (1988) and L. C. Tsui, Human Mutat., 1:197-203 (1992)), and the study of drug metabolism and oncogenic mutations (Hollstein et al., Science, 253:49-53 (1991)). In addition, the cost-effectiveness of nucleic acid analysis, such as for infectious disease diagnosis, varies directly with the multiplex scale in panel testing. Many of these applications depend on the discrimination of single-base differences at a multiplicity of sometimes closely spaced loci.

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample is fractionated by gel electrophoresis, and then fixed on a nitrocellulose filter. By reacting the filter with one or more labeled probes under hybridization conditions, the presence of bands containing the probe sequences can be identified. The method is especially useful for identifying fragments in a restriction-enzyme DNA digest which contains a given probe sequence and for analyzing restriction-fragment length polymorphisms ("RFLPs").

Another approach to detecting the presence of a given sequence or sequences in a polynucleotide sample involves selective amplification of the sequence(s) by polymerase chain reaction. U.S. Pat. No. 4,683,202 and R. K. Saiki, et al., Science 230:1350 (1985). In this method, primers complementary to opposite end portions of the selected sequence(s) are used to promote, in conjunction with thermal cycling, successive rounds of primer-initiated replication. The amplified sequence(s) may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported. U.S. Pat. No. 4,883,750, D. Y. Wu, et al., Genomics 4:560 (1989), U. Landegren, et al., Science 241:1077 (1988), and E. Winn-Deen, et al., Clin. Chem. 37:1522 (1991). In one approach, known as oligonucleotide ligation assay ("OLA"), two probes or probe elements which span a target region of interest are hybridized to the target region. Where the probe elements basepair with adjacent target bases, the confronting ends of the probe elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction. When two complementary pairs of probe elements are utilized, the process is referred to as the ligase chain reaction which achieves exponential amplification of target sequences. F. Barany, Proc. Nat'l Acad. Sci. USA, 88:189-93 (1991) and F. Barany, PCR Methods and Applications, 1:5-16 (1991).

Another scheme for multiplex detection of nucleic acid sequence differences is disclosed in U.S. Pat. No. 5,470,705 where sequence-specific probes, having a detectable label and a distinctive ratio of charge/translational frictional drag, can be hybridized to a target and ligated together. This technique was used in Grossman, et al., Nucl. Acids Res. 22(21):4527-34 (1994) for the large scale multiplex analysis of the cystic fibrosis transmembrane regulator gene. Jou, et al., Human Mutation 5:86-93 (1995) relates to the use of a so called "gap ligase chain reaction" process to amplify simultaneously selected regions of multiple exons with the amplified products being read on an immunochromatographic strip having antibodies specific to the different haptens on the probes for each exon.

Ligation of allele-specific probes generally has used solid-phase capture (U. Landegren et al., Science, 241:1077-1080 (1988); Nickerson et al., Proc. Natl. Acad. Sci. USA, 87:8923-8927 (1990)) or size-dependent separation (D. Y. Wu, et al., Genomics, 4:560-569 (1989) and F. Barany, Proc. Natl. Acad. Sci, 88:189-193 (1991)) to resolve the allelic signals, the latter method being limited in multiplex scale by the narrow size range of ligation probes. Further, in a multiplex format, the ligase detection reaction alone cannot make enough product to detect and quantify small amounts of target sequences. The gap ligase chain reaction process requires an additional step—polymerase extension. The use of probes with distinctive ratios of charge/translational frictional drag for a more complex multiplex will either require longer electrophoresis times or the use of an alternate form of detection.

Methods for efficiently and accurately sequencing long nucleic acid fragments are needed. There is a great need for rapid, high-throughput, and low cost sequencing technology, such as for point-of-care applications and field detection of pathogens. The present invention permits sequencing of large amount of genome using simple chemistry and low cost equipments that lead to significant cost reduction and increase in speed, and other related advantages as well.

SUMMARY OF THE INVENTION

Provided herein are methods and systems for sequencing a target nucleic acid. In one embodiment, the method comprises: (a) sequencing one or more bases of a target nucleic acid by extending a first sequencing primer hybridized to the target nucleic acid to generate a first primer extension product, thereby obtaining a first sequence read; (b) releasing the first primer extension product from the target nucleic acid; (c) hybridizing a second sequencing primer to the target nucleic acid; (d) generating a second primer extension product (extended primer) by extending the second sequencing primer through limited extension; and (e) sequencing one or more bases of the target nucleic acid by further extending the second primer extension product to generate a third primer extension product, thereby obtaining a second sequence read.

In one embodiment, the first sequencing primer and second sequencing primer are the same. In another embodiment, the first sequencing primer and second sequencing primer are different.

The limited extension can be carried out or performed by pulse extension, such as, by allowing the extending reaction to last for a short period of time, such as less than a minute or from approximately half a minute to a minute, such as from 1-5, 5-10, 10-30, 30 to 60 seconds. In some embodiments, limited extension can be performed by extension and wash cycles.

The limited extension can be carried out by using a nucleic acid polymerase and one or more sets of nucleotides. The one or more sets can each comprise no more than three different nucleotides. The extending can be with more than one set of nucleotides, such as at least 1, 2, 3, or more sets. A set of nucleotides can comprise one, two or three different nucleotides.

In one embodiment, the method further comprises obtaining one or more additional sequence reads, such as by repeating the steps of releasing a primer extension product from the target nucleic acid; hybridizing an additional sequencing primer to the target nucleic acid; generating an additional primer extension product by extending the additional sequencing primer through limited extension; and sequencing one or more bases of the target nucleic acid by further extending the additional primer extension product to generate an additional primer extension product, thereby obtaining an additional sequence read. The sequence of the target nucleic acid can be determined by assembling the first, second, and optional, one or more additional sequence reads. The sequencing of the target nucleic acid can be by extending the sequencing primer using a labeled reversible terminator, ligation, or any other methods known in the art.

In another embodiment, a washing step or nucleotide degradation step can be performed prior to a subsequent addition of a set of nucleotides.

The target nucleic acid can be attached to a substrate. The substrate can be a flat surface or bead, such as a flow cell. In another embodiment, the substrate can comprise glass. In another embodiment, the target nucleic acid can be attached to the substrate via a capture probe.

The methods and systems disclosed herein can further comprise analyzing the sequencing results, such as generated by a method disclosed herein, to provide a diagnosis, prognosis, or theranosis for a subject.

Furthermore, a method disclosed herein can be used to sequence a plurality of target nucleic acids.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts an example of a template and triple base extension reactions. FIG. 1 discloses SEQ ID NOS 1-11, respectively, in order of appearance.

FIG. 2 depicts an exemplary embodiment of a dark base (native nucleotide) extension experiment design.

DETAILED DESCRIPTION OF THE INVENTION

Figure 3:
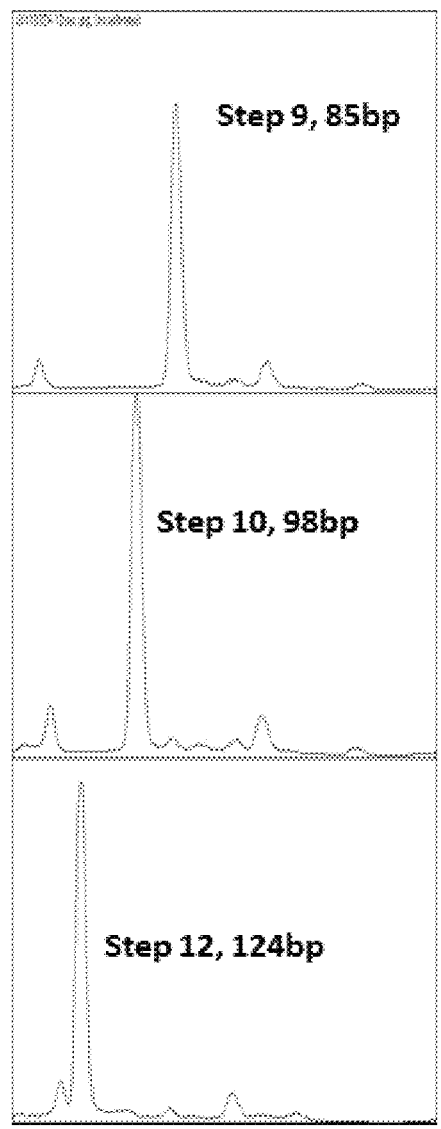
FIG. 3 depicts results of an exemplary embodiment of the present invention, in which 12 steps of 3-base extension resulted in a 124 base pair (bp) product (extension plus primer), wherein the template was an oligonucleotide.

Unless defined otherwise, all technical and scientific terms used herein have the same meaning as commonly understood by one of ordinary skill in the art to which this present invention belongs. Although any methods and materials similar or equivalent to those described herein can also be used in the practice or testing of the present invention, representative illustrative methods and materials are now described. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000), Lehninger, (2004) Principles of Biochemistry $4^{th}$ Ed., W.H. Freeman Pub., New York, N.Y. and Berg et al. (2006) Biochemistry, 6th Ed., W.H. Freeman Pub., New York, N.Y., all of which are herein incorporated in their entirety by reference for all purposes.

Provided herein are methods and systems for sequencing a target nucleic acid. In one aspect of the present invention, a method for sequencing nucleic acids, such as long nucleic acid fragments, is performed in parallel. For example, the sequencing method disclosed herein includes controlled primer extension to certain length (or length distribution) and then sequencing a nucleic acid target using extended primers. In another aspect of the present invention, a nucleic acid template is sequenced by a set of staggered primers of different length.

In one embodiment, a series of parallel reactions is performed such that each reaction extends a primer, such as a deoxyribonucleic acid (DNA) primer or sequencing primer, to a different length to create incremental sequences complementary to a sequencing template (the target nucleic acid or target polynucleotide molecule). The extension of the primer or sequencing primer can be with one or more nucleotides and a polymerase, such as native or native performance nucleotide(s) and native or native performance polymerase. These incremental sequences can be generated or produced by extending the sequencing primer through limited extension, such as by pulse extension. In another embodiment, incremental sequences can be generated or produced by extending the sequencing primer through limited (or controlled) extension, such as with sets of nucleotides comprising no more than three different nucleotides with an optional washing step between steps. The washing solution may optionally include nucleotide degrading enzymes such as apyrase and/or alkaline phosphatase. Alternatively, limited extension can be pulse extension with no washing steps between extension steps where extension is performed with serial addition of various sets of nucleotides, wherein each set comprises one, two or three different nucleotides. In a pulse mode, nucleotide combinations are typically added serially at specified time intervals (such as 1-10, 10-20, 20-30, 30-60 seconds). The nucleotides are typically degraded before the next addition of nucleotides by nucleotide degrading enzymes such as apyrase and/or alkaline phosphatase. Extension with washing and pulse extension steps can be combined. For example, extension can be performed in a pulse mode After certain number of pulse extension steps (such as 20-40, 41-60, 61-100 steps), the reaction mixture can be washed to remove residual nucleotides or by products. A new series of pulse extension steps can then be performed.

The extended primers, or primer extension products, can then be used as sequencing primers to determine the sequence of the template. For example, a primer extension product can be extended with in the presence of labeled nucleotides to generate a sequence read for the template. Sequencing can be performed using, for example, reversible terminator sequencing, ligation based sequencing, pyrophosphate detection based sequencing, proton detection based sequencing.

In one embodiment, sequencing a target nucleic acid is through incremental base extension, compiling data generated from detecting the presence of bases present in each gradually extended sequence, and determining the sequence of the target nucleic acid through analyzing the data collected. For example, a plurality of primer extension products of varying lengths are generated or produced for a template. The plurality of primer extension products can then be used to produce a variety of sequence reads. The sequence of the target polynucleotide molecule can then be obtained by assembling the variety of sequence reads.

In one aspect of the present invention, the method comprises sequencing one or more bases of a target nucleic acid by using a first sequencing primer hybridized to a target nucleic acid. Such sequencing can be performed by sequencing by synthesis, for example, step-wise reversible terminator sequencing, incorporating labeled nucleotides, pyrophosphate detection based sequencing, ion detection based sequencing, or alternatively, step wise ligations, or other methods, thereby obtaining a first sequence read. The first primer and any extension from the primer from the first sequencing can then be released from the target nucleic acid, for example, by denaturing the target nucleic acid via heating the target nucleic acid, contacting the target nucleic acid with sodium hydroxide solution, urea solution, formamide solution, etc. The target nucleic acid is then hybridized to a second sequencing primer which can be the same as the first sequencing primer. A primer extension product is generated by extending the second sequencing primer, such as through controlled limited extension to produce an elongated primer, and the elongated primer is used to sequence one or more bases of the target nucleic acid by using many sequencing methods such as step-wise reversible terminator sequencing from the elongated primer, incorporating labeled nucleotides, pyrophosphate detection based sequencing, ion detection based sequencing, step wise ligations, or other methods, thereby obtaining a second sequence read. The steps of releasing the primer extension product, hybridizing a sequencing primer, extending the sequencing primer to produce an elongated primer, and extending the elongated primer product to obtain a sequence read can be repeated for many times. When these steps are repeated, the controlled extension length may be different. The plurality of sequence reads can be assembled, such as through overlapping sequence reads, to generate the sequence of the target nucleic acid.

For example, if the second primer extension product is shorter than the first sequence read, there will be an overlapping sequence between the first sequence read and second sequence read. If the second primer extension product is longer than the first sequence read, there can be a gap between the first sequence read and the second sequence read. However, additional sequence reads, such as to fill such a gap, can be obtained with subsequent extension product removal(s) and one or more new rounds of primer extension to obtain additional sequence reads. Fewer extension steps may be used to have more overlapping sequence results between successive sequencing for more templates. Alternatively, more extension steps can be used to have more non-overlapping sequences.

In general, the length of first sequence read and subsequent reads depend on the sequencing technology used, which generate different lengths for a given confidence. Preferably, the sequence read is between 25 to 150 bp, or up to 1 kb.

In some embodiments, a large number of nucleic acid targets are simultaneously sequenced. In such embodiments, the target nucleic acids are typically immobilized on a substrate. At least some target nucleic acids can be spatially separated by forming single molecule clusters that are at least partially non overlapping.

Target

In one aspect, the present invention provides a method for sequencing a target nucleic acid molecule. By "target nucleic acid molecule", "target molecule", "target polynucleotide", "target polynucleotide molecule" or grammatically equivalent thereof, herein is meant a nucleic acid of interest.

In one aspect, a target nucleic acid is genomic DNA derived from the genetic material in the chromosomes of a particular organism is genomic DNA. A genomic library is a collection of clones made from a set of randomly generated overlapping DNA fragments representing the entire genome of an organism. Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification using methods known in the art, including without limitation extracting a fragment of genomic DNA from an organism (e.g. a cell or bacteria) to obtain target nucleic acids. In another example, target nucleic acids can also be isolated by amplification using methods known in the art, including without limitation polymerase chain reaction (PCR), whole genome amplification (WGA), multiple displacement amplification (MDA), rolling circle amplification (RCA), rolling circle amplification (RCR) and other amplification methodologies. Target nucleic acids may also be obtained through cloning, including cloning into vehicles such as plasmids, yeast, and bacterial artificial chromosomes. Target nucleic acids may also have an exogenous sequence, such as a universal primer sequence or barcode sequence introduced during the amplification process. The term "sequencing template" used herein may refer the target nucleic acid itself or to a nucleotide sequence that is identical to the nucleotide sequence of a fragment of a target nucleic acid. In one embodiment, the target nucleic acid molecule comprises ribonucleic acid (RNA).

In one embodiment, the target polynucleotide is genomic DNA or a portion of the genomic DNA. While one embodiment is for sequencing a whole genome, such as at more than 50% coverage, these embodiments are also suitable for sequencing a targeted region such as genomic regions relating to drug metabolism. In one example, the target polynucleotide is human genomic DNA.

"Nucleic acid" or "oligonucleotide" or "polynucleotide" or grammatical equivalents typically refer to at least two nucleotides covalently linked together. A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (see e.g. Beaucage et al., Tetrahedron 49(10): 1925 (1993); Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 (1986)), phosphorothioate (Mag et al., Nucleic Acids Res. 19:1437 (1991); and U.S. Pat. No. 5,644,048), phosphorodithioate (see e.g. Briu et al., J. Am. Chem. Soc. 111:2321 (1989)), O-methylphophoroamidite linkages (see e.g. Eckstein, Oligonucleotides and Analogues: A Practical Approach, Oxford University Press), and peptide nucleic acid (also referred to herein as "PNA") backbones and linkages (see e.g. Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996)).

Other analog nucleic acids include those with bicyclic structures including locked nucleic acids, also referred to herein as "LNA", (see e.g. Koshkin et al., J. Am. Chem. Soc. 120.13252 3 (1998)); positive backbones (Denpcy et al., Proc. Natl. Acad. Sci. USA 92:6097 (1995)); non-ionic backbones (see e.g. U.S. Pat. Nos. 5,386,023, 5,637,684, 5,602,240, 5,216,141 and 4,469,863; Kiedrowshi et al., Angew. Chem. Intl. Ed. English 30:423 (1991)); Letsinger et al., J. Am. Chem. Soc. 110:4470 (1988); Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook.

Nucleic acids containing one or more carbocyclic sugars are also included within the definition of nucleic acids (see e.g. Jenkins et al., Chem. Soc. Rev. (1995) pp 169 176). Several nucleic acid analogs are described in Rawls, C & E News Jun. 2, 1997 page 35.

The target nucleic acids may be single stranded or double stranded, as specified, or contain portions of both double stranded or single stranded sequence. Depending on the application, the nucleic acids may be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

In one embodiment, the methods of the present invention comprise capture of target polynucleotide. The target polynucleotide may be from a known region of the genome. In one embodiment, oligonucleotide probes can be immobilized on beads and these oligonucleotide beads which are inexpensive and reusable can be used to capture the target genomic polynucleotide. In another embodiment, microarrays are used to capture target polynucleotide.

In one embodiment, the target polynucleotide may be fragmented to a suitable length or plurality of suitable lengths, such as approximately between 100-200, 200-300, 300-500, 500-1000, 1000-2000 bases in length.

In one embodiment, the target polynucleotide is prepared by whole genome amplification (WGA) (see for example, Hawkins et al.: Whole genome amplification—applications and advances. Curr. Opin. Biotechnol. 2002 February; 13(1): 65-7)). In another embodiment, the target polynucleotide is prepared by whole genome sampling assay (WGSA). Generally, the WGSA reduces the complexity of a nucleic acid sample by amplifying a subset of the fragments in the sample. A nucleic acid sample is fragmented with one or more restriction enzymes and an adapter is ligated to both ends of the fragments. A primer that is complementary to the adapter sequence is used to amplify the fragments using PCR. During PCR fragments of a selected size range are selectively amplified. The size range may be, for example, 400-800 or 400 to 2000 base pairs. Fragments that are outside the selected size range are not efficiently amplified. The fragments that are amplified by WGSA may be predicted by in silico digestion and an array may be designed to genotype SNPs that are predicted to be amplified. Genotyping may be done by allele specific hybridization with probes that are perfectly complementary to individual alleles of a SNP. A set of probes that are complementary to the region surrounding each SNP may be present on the array. Perfect match (PM) probes are complementary to the target over the entire length of the probe. Mismatch (MM) probes are identical to perfect match probes except for a single mismatch base. The mismatch position is typically the central position. WGSA is disclosed in Kennedy et al. (2003), *Nat Biotechnol*, Vol., pp. 1233-1237, and U.S. patent application Ser. Nos. 10/316,517, 10/442,021, 10/463,991, 10/316,629 and U.S. Pat. Nos. 6,361,947, 6,548,810, 7,267,966, 7,297,778, and 7,300,788, all of which are herein incorporated by reference. WGSA can simultaneously genotype more than 10,000 SNPs in parallel by allele-specific hybridization to perfect match and mismatch probes synthesized on an array. WGSA may not be able to assay the entire panels of loci.

In one embodiment, the target polynucleotide is prepared by PCR, such as long-range PCR. Long range PCR allows the amplification of PCR products, which are much larger than those achieved with conventional Taq polymerases. Generally, up to 27 kb fragments from good quality genomic DNA can be prepared, although 10-20 kb fragments are routinely achievable, given the appropriate conditions. In some embodiments, a fragment greater than 27 kb is obtained. The method typically relies on a mixture of thermostable DNA polymerases, usually Taq DNA polymerase for high processivity (i.e. 5'-3' polymerase activity) and another DNA polymerase with 3'-5' proofreading abilities (usually Pwo). This combination of features allows longer primer extension than can be achieved with Taq alone.

In one embodiment, the target polynucleotide is prepared by locus-specific multiplex PCR. Multiplex locus specific amplification can be used to amplify a plurality of preselected target sequences from a complex background of nucleic acids. The targets are selected for amplification using splint oligonucleotides that are used to modify the ends of the fragments. The fragments have known end sequences and the splints are designed to be complementary to the ends. The splint can bring the ends of the fragment together and the ends are joined to form a circle. The splint can also be used to add a common priming site to the ends of the target fragments. Specific loci are amplified and can be subsequently analyzed.

In yet another embodiment, target polynucleotides are produced using multiplex PCR and each of the PCR fragments is labeled with a tag sequence. Such tag sequence can be added as a part of one of the primers used for the PCR. Therefore, each resulting PCR fragment can be uniquely identified. Such applications can be useful for the identification of species, such as microbial species.

Other suitable amplification methods include but are not limited to the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603 each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference. Additional methods of sample preparation and techniques for reducing the complexity of a nucleic sample are described in Dong et al., Genome Research 11, 1418 (2001), in U.S. Pat. Nos. 6,361,947, 6,391,592, 6,632,611, 6,872,529, 6,958,225 and U.S. Ser. No. 09/916,135.

Naturally-existing targets can be assayed directly in cell lysates, in nucleic acid extracts, or after partial purification of fractions of nucleic acids so that they are enriched in targets of interest. In one example, the target polynucleotide is human genomic DNA. The polynucleotide target to be detected can be unmodified or modified. Useful modifications include, without limitation, radioactive and fluorescent labels as well as anchor ligands such as biotin or digoxigenin. The modification(s) can be placed internally or at either the 5' or 3' end of the targets. Target modification can be carried out post-synthetically, ether by chemical or enzymatic reaction such as ligation or polymerase-assisted extension. Alternatively, the internal labels and anchor ligands can be incorporated into an amplified target or its complement directly during enzymatic polymerization reactions using small amounts of modified NTPs as substrates.

The target polynucleotide can be isolated from a subject. The subject is not limited to a human being but may also be other organisms including but not limited to mammals, plants, bacteria, virus or fungi. In one example, the target polynucleotide is genomic DNA extracted from a human.

Sequencing Primer

A sequencing primer, such as a non-extended sequencing primer or primer extension product (such as an extended primer) that is further extended and used as a sequencing primer, can be used to sequence one or more bases, such as at least 1, 2, 3, 4, 5, 6, 7, 8, 9, 10, 20, 25, 35, 50, 75, 100, 125, or 150 bases, or about 1, 5, 10, 20, 25, 35, 50, 75, 100, 125, or 150 bases. In some embodiments, longer sequencing primers such as primers of 500-1000, 1000-5000, 5,000-10,000 bases can be used.

In one embodiment, a single sequencing primer is used for extension. For example, a first sequencing primer hybridized to a target nucleic acid is extended to obtain a first sequence read. The first primer extension product can then be released from the target nucleic acid. The target nucleic acid can be hybridized to the same sequencing primer. An extended primer can then be generated or produced by extending the same sequencing primer, such as through limited extension, and sequencing one or more bases of the target nucleic acid by further extending the extended primer to obtain a second sequence read. In such an embodiment, a target nucleic acid can be constructed to allow the hybridization of a single primer, such as by adding a capture probe or sequence complementary to the primer to an end of the target template, as further described herein. In one embodiment, the target nucleic acid is attached to a substrate via a capture probe.

In another embodiment, different sequencing primers are used for extension. For example, a first sequencing primer hybridized to a target nucleic acid is extended to generate a first primer extension product, thereby obtaining a first sequence read. The first primer extension product can then be released from the target nucleic acid. The target nucleic acid can be hybridized to a different sequencing primer. The different sequencing primer can of the same sequence as the first primer or of a different sequence than the first primer. A second primer extension product can then be generated or produced by extending the different sequencing primer, such as through limited extension, and sequencing one or more bases of the target nucleic acid by further extending the second primer extension product to generate a third primer extension product, thereby obtaining a second sequence read. In such an embodiment, a target nucleic acid can be constructed to allow the hybridization of a single primer, such as by adding a capture probe or sequence complementary to the primer to an end of the target template. In one embodiment, the target nucleic acid is attached to a substrate via a capture probe.

Controlled Base Extension

Base extension or dark base extension or controlled base extension, where unlabelled nucleotides are used to extend the length of a primer, can be used to increase the length of a sequencing primer. Dark base extension can be used to extend a primer in a massively parallel fashion and subsequently the extended primer can be used to sequence their corresponding template. As a plurality of extended primers of varying length can be generated, the corresponding sequence reads from the primers differ. For example, a first primer extension product (i.e. a first extended primer) and a second primer extension product (i.e. a second extended primer) are generated from the same sequencing primer (i.e. a non-extended primer). The second extended primer is extended longer than the first extended primer, thus, the second extended primer produces a sequence read that is further downstream on a target template than a sequence read generated from a first extended primer. Thus, sequence read length can be increased by successive sequencing the same template with primers of different lengths created by dark base extension.

In one embodiment, a native base extension reaction is carried out to extend the sequencing primer. Native base extension can be performed using a polymerase in a buffer that is suitable for the polymerase to catalyze polymerase reaction. In addition to the polymerase, nucleotide(s) are also added to the extension reaction. In one embodiment, a reaction contains a polymerase and a set of nucleotides, wherein the set of nucleotides comprises no more than three different nucleotides. For example, the set of nucleotides comprises one to three of the four types of nucleotides (for DNA polymerase, one, two or three of the four nucleotides dATP, dCTP, dTTP, dGTP). In one embodiment, a reaction containing three of the different nucleotides stops at the template base that is complementary to the missing nucleotide. For example, for a reaction that has dATP, dCTP, dGTP, the extension stops at a base "A" on the template because "A" is complementary to the missing nucleotide dTTP, thereby limiting extension of a primer hybridized to the template.

Base extension can be done many times with various nucleotide sets, or with numerous cycles of nucleotide sets. For example, a set of three different nucleotides can be 1) dATP, dCTP, dGTP; 2) dCTP, dGTP, dTTP; 3) dGTP, dTTP, dATP; or 4) dTTP, dATP, dCTP, and a primer can be extended with one or more sets in a cycle. As a minimum, two sets of different nucleotide combinations, such as a first set of dATP, dCTP, dGTP and a second set of dCTP, dGTP, dTTP can be used in a cycle to control the extension length. Similarly, a two nucleotide set or one nucleotide set can also be used and cycled in extending a primer. A combination of one or more three nucleotide sets, one or more two nucleotide sets or one or more one nucleotide sets may also be used in some embodiments. Base extension by a method disclosed herein can be used to provide limited extension of a primer, such that elongation of the primer(s) is performed with some control of the extension length. Reversible terminators with or without labels may also be used to extend the primer using an extension, deprotection and extension cycle.

In one embodiment, polymerase in its suitable buffer is then added to make contact with the target nucleic acid. The buffer may contain a set of nucleotides (1-3 nucleotides) or the set of nucleotides can be added later to start the reaction. After a suitable amount of time (such as approximately 5, 10, 30 to 90 second for native bases), the buffer solution is removed and template is washed to remove the nucleotides. Optionally, nucleotide degrading enzymes such as apyrase or alkaline phosphatase are added into the reaction buffer at the end of the reaction and/or in the washing solution to minimize contamination of the next round of extension with nucleotides from the previous extension.

Alternatively, base extension can be performed using a pulse method. In such a method, a template is contacted with a multi-enzyme buffer that contains a polymerase (such as Klenow exo(−) for DNA sequencing), one or several nucleotide degrading enzymes such as apyrase, alkaline phosphatase. Optionally, an inorganic pyrophosphatase is added to degrade pyrophosphate generated by polymerase reaction. Sets of nucleotides can be successively added to the reaction buffer at interval of several seconds, 5-10 seconds, 10-20 seconds, 20-30 seconds, or 30-90 seconds. In some embodiments, the time of extension is optimized to allow the extension of 5, 10, 20, 30, 40, 50, 60, 70, 80, 90, 100 bases, or longer. Nucleotides are utilized by the polymerase for polymerase reaction and at the same time, are degraded by apyrase or alkaline phosphatase.

Release

One or more extension products of the sequencing reactions can be released from a target nucleic acid, thereby allowing a subsequently added primer to hybridize to the target nucleic acid. Removal or release of an extension product can be carried out by denaturing and washing the extension products. Denaturing can be performed by applying heat or electric current, adding NaOH solution, formamide solution or urea solution, or other methods known in the art. A new sequencing primer or a set of new sequencing primers can then hybridize with the template. The new sequencing primer can be the same primer used in the first sequencing reaction. The new sequencing primer can be of, or comprises, the same sequence as the primer used in the first sequencing reaction.

Sequencing

Sequencing by extending a first sequencing primer or by extending a primer extension product can be carried out using a variety of methods. For example, sequencing can be carried out with a labeled reversible terminator or by ligation with a labeled oligonucleotide. Sequencing can be performed using any commercially available method, such as a reversible terminator based sequencing method that is commercially available from companies such as Illumina, Inc. (San Diego, Calif.).

In one embodiment, sequencing can be conducted with labeled nucleotides such as dNTPs with labels. Bases may be detected by extending the incremental fragments via contacting the hybridization complexes sequentially with one of labeled dATP, dCTP, dGTP and dTTP, in the presence of a polymerase, and detecting the incorporation of the labeled dATP, dCTP, dGTP and dTTP to obtain a sequence read from each reaction.

In one embodiment, a mixture of labeled dATP, dCTP, dGTP and dTTP are used. Generally, due to general low incorporation efficiency of the modified dNTPs, such as labeled dNTPs, only the first few bases are extended to generate strong signal. The possibility of "run-on" extension is rather low and the signal generated by such "run-on" extension can be filtered out as noise using methods provided herein or known in the art. In one embodiment, a mixture of labeled ddATP, ddCTP, ddGTP and ddTTP are used, and no "run-on" extension is permitted. In one embodiment, only one round of interrogation that covers all four possible bases is carried for each incremental fragment. For example, sequential addition with one labeled dNTP in each round of interrogation provides possible addition of one detectable base at a time (i.e. on each substrate). This generally results in short read (such as one base or a few bases) that could be assembled for each round. In another embodiment, a longer read is generated with more than one round of interrogation.

In another embodiment, a mixture of labeled ddATP, ddCTP, ddGTP, ddTTP and small amount (<10% (e.g. 5, 6, 7, 8, or 9%) or <20% (e.g., 10, 11, 12, 13, 14, 15, 16, 17, 18, or 19%) of native dATP, dCTP, dGTP, and dTTP are added.

In one embodiment, the labeled nucleotides are reversible terminators. Multiple bases can be detected by the signal strength or in the case of reversible terminator, base addition detection. Nucleotide reversible terminators are nucleotide analogues, which are modified with a reversible chemical moiety capping the 3'-OH group to temporarily terminate the polymerase reaction. In this way, generally only one nucleotide is incorporated into the growing DNA strand even in homopolymeric regions. For example, the 3' end can be capped with an amino-2-hydroxypropyl group. An allyl or a 2-nitrobenzyl group can also be used as the reversible moiety to cap the 3'-OH of the four nucleotides. Examples of reversible terminators include but are not limited to 3'-O-modified nucleotides such as 3'-O-allyl-dNTPs and 3'-O-(2-nitrobenzyl)-dNTPs.

In one embodiment, after detection of the cleavage site present on the solution probe, the 3'-OH of the primer extension products is regenerated through different deprotection methods. The capping moiety on the 3'-OH of the DNA extension product can be efficiently removed after detection of a cleavage site by a chemical method, enzymatic reaction or photolysis, i.e. the cap will be cleaved from the cleavage site. To sequence DNA, in one embodiment, templates containing homopolymeric regions are immobilized on Sepharose beads, and then extension—signal detection—deprotection cycles are conducted by using the nucleotide reversible terminators on the DNA beads to unambiguously decipher the sequence of DNA templates. In one embodiment, this reversible-terminator-sequencing approach is used in the subject methods to accurately determine DNA sequences. (The cap may be referred to herein as a "protective group").

Polynucleotide of the invention can be labeled. In one embodiment, a molecule or compound has at least one detectable label (e.g., isotope or chemical compound) attached to enable the detection of the compound. In general, labels of use in the present invention include without limitation isotopic labels, which may be radioactive or heavy isotopes, magnetic labels, electrical labels, thermal labels, colored and luminescent dyes, enzymes and magnetic particles as well. Labels can also include metal nanoparticles, such as a heavy element or large atomic number element, which provide high contrast in electron microscopy. Dyes of use in the invention may be chromophores, phosphors or fluorescent dyes, which due to their strong signals provide a good signal-to-noise ratio for decoding.

In one embodiment, labels may include the use of fluorescent labels. Suitable dyes for use in the present invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, and others described in the 11th Edition of the Molecular Probes Handbook by Richard P. Haugland, hereby expressly incorporated by reference in its entirety. Commercially available fluorescent nucleotide analogues readily incorporated into the labeling oligonucleotides include, for example, Cy3-dCTP, Cy3-dUTP, Cy5-dCTP, Cy5-dUTP (GE Healthcare), fluorescein-12-dUTP, tetramethylrhodamine-6-dUTP, Texas Red®-5-dUTP, Cascade Blue®-7-dUTP, BODIPY® FL-14-dUTP, BODIPY®R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, and Alexa Fluor® 546-14-UTP (Invitrogen). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Invitrogen), and Cy2, Cy3.5, Cy5.5, and Cy7 (GE Healthcare).

In one embodiment, multiplex detection formats are used for base detection or sequencing. Examples of multiplex formats that can be used include, but are not limited to, either labeled/tagged bead sets (e.g., those produced by Luminex), in which each label is assigned to the individual probe-specific primer, or oligonucleotide arrays on slides, in which specific oligonucleotide spot/position is assigned to the individual probe-specific primer. The limited sequence complexity of the recovered target-specific probes can provide conditions for easier and higher level multiplexing, especially using with universal and Zip-code/ID sequence tags. After the hybridization of the primers to the target-probe complex, the primers can be extended by a nucleotide polymerase. In certain embodiments, the polymerase is selected from an RNA polymerase and a reverse transcriptase.

Where an array is utilized, the detection phase of the process may involve scanning and identifying target polynucleotide sequences in the test sample. Scanning can be carried out by scanning probe microscopy (SPM) including scanning tunneling microscopy (STM) and atomic force microscopy (AFM), scanning electron microscopy, confocal microscopy, charge-coupled device, infrared microscopy, electrical conductance, transmission electron microscopy (TEM), and fluorescent or phosphor imaging, for example fluorescence resonance energy transfer (FRET). Optical interrogation/detection techniques include but are not limited to near-field scanning optical microscopy (NSOM), confocal microscopy and evanescent wave excitation. More specific versions of these techniques include far-field confocal microscopy, two-photon microscopy, wide-field epi-illumination, and total internal reflection (TIR) microscopy. Many of the above techniques can also be used in a spectroscopic mode. The actual detection means include charge coupled device (CCD) cameras and intensified CCDs, photodiodes and photomultiplier tubes. These methods and techniques are well-known in the art. Various detection methods are disclosed in U.S. Patent Application Publication No. US 2004/0248144, which is herein incorporated by reference.

For multicolor imaging, signals of different wavelength can be obtained by multiple acquisitions or by simultaneous acquisition by splitting the signal, using RGB detectors or analyzing the whole spectrum (Richard Levenson, Cambridge Healthtech Institutes, Fifth Annual meeting on Advances in Assays, Molecular Labels, Signaling and Detection, May 17-18$^{th}$ Washington D.C.). Several spectral lines can be acquired by the use of a filter wheel or a monochromater. Electronic tunable filters such as acoustic-optic tunable filters or liquid crystal tunable filters can be used to obtain multispectral imaging (e.g. Oleg Hait, Sergey Smirnov and Chieu D. Tran, 2001, Analytical Chemistry 73: 732-739). An alternative method to obtain a spectrum is hyperspectral imaging (Schultz et al., 2001, Cytometry 43:239-247).

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, 7,689,022 and in WO99/47964, each of which also is hereby incorporated by reference in its entirety for all purposes. Fluorescence imaging and software programs or algorithms for DNA sequence analysis and read interpretation are known to one of ordinary skill in the art and are disclosed in Harris T D, et al. "Single-Molecule DNA Sequencing of a Viral Genome" Science 4 Apr. 2008: Vol. 320. no. 5872, pp. 106-109, which is herein incorporated by reference in its entirety. In one embodiment, Phred software is used for DNA sequence analysis. Phred reads DNA sequencer trace data, calls bases, assigns quality values to the bases, and writes the base calls and quality values to output files. Phred is a widely-used program for base calling DNA sequencing trace files. Phred can read trace data from SCF files and ABI model 373 and 377 DNA sequencer chromat files, automatically detecting the file format. After calling bases, Phred writes the sequences to files in either FASTA format, the format suitable for XBAP, PHD format, or the SCF format. Quality values for the bases are written to FASTA format files or PHD files, which can be used by the phrap sequence assembly program in order to increase the accuracy of the assembled sequence. The quality value is a log-transformed error probability, specifically $Q=-10 \log_{10}(P_e)$ where Q and $P_e$ are respectively the quality value and error probability of a particular base call. The Phred quality values have been thoroughly tested for both accuracy and power to discriminate between correct and incorrect base-calls. Phred can use the quality values to perform sequence trimming.

In one embodiment, one detection cycle is performed by adding labeled A, C, G, T sequentially followed by washing and detecting after each addition. In one embodiment, multiple detection cycles can be performed using nucleotides with removable labels.

In one embodiment, the series of incremental fragments are further extended (thus, serving as sequencing primer) for sequencing reactions to obtain the sequence information of the target molecules. The sequence information is a series fragment sequences that are adjacent on the target molecule, which can be assembled to obtain a long fragment or the full length sequence of the target molecule.

In one embodiment of the present invention, serial sequencing of a target polynucleotide is converted to parallel sequencing to reduce the time required for sequencing a given number of bases of the target polynucleotide.

Immobilized Target

In one embodiment, a nucleic acid target is attached to a substrate or immobilized on a substrate. The substrate can be a bead, flat substrate, flow cell or other suitable surfaces. In one embodiment, the substrate comprises glass.

In one embodiment, a target nucleic acid is attached or immobilized to a substrate via a capture probe. A capture probe is an oligonucleotide that is attached to the surface of a substrate and is capable to bind to a sequencing template. Capture probes can be of various lengths, such as from 18 bases to 100 bases, such as 20 bases to 50 bases.

In one embodiment, the capture probe has a sequence that is complementary to the sequencing template. For example, if the present method is used to sequence a genome with at least partial sequence known already, capture probes can be designed to complement to the known sequences. In one embodiment, the capture probes are complementary to "barcode" or "identifier" sequence added to the sequencing templates via, e.g., specific ligation, as a part of the primer for PCR reaction. In such reactions, a sequencing template-specific primer and a primer comprising a unique barcode are used for the amplification, thus all the target molecules with the same sequences have the same barcode attached.

The capture probe can be attached to the substrate at either the 5' end or the 3' end. In some embodiments, the capture probe is attached to the substrate at the 5' end, and the 3' end of the capture probe can be extended by the incorporation of nucleotides as described herein to generate incremental extension fragments which can in turn be sequenced by further incorporation of labeled nucleotides. In another embodiment, the capture probe is attached to the substrate at the 3'end, and the 5' end of the capture probe cannot be extended by the incorporation of nucleotides. A second probe (or sequencing primer) hybridizes to the sequencing template and its 3' end is extended by the incorporation of nucleotides as described herein to generate an incremental extension fragment which can in turn be sequenced by further incorporation of labeled nucleotides. In this case, the extension is towards the direction of the capture probe. In general, the sequencing primer hybridizes to a linker introduced to the end of the sequencing template when generated, either directly from a genomic DNA or from a parent target molecule. Thus the sequencing primer is a "universal primer" that can be used to sequence different target molecules. In one embodiment, sequencing primers specific to the target molecule are used.

In one embodiment, the capture probe is immobilized on a solid support before binding to the sequencing template. In one embodiment, the 5' end of a capture probe is attached to a solid surface or substrate. A capture probe can be immobilized by various methods known in the art including, without limitation, covalent cross-linking to a surface (e.g., photochemically or chemically), non-covalent attachment to the surface through the interaction of an anchor ligand with a corresponding receptor protein (e.g. biotin-streptavidin or digoxigenin-anti-digoxigenin antibody), or through hybridization to an anchor nucleic acid or nucleic acid analog. The anchor nucleic acid or nucleic acid analog have sufficient complementarity to the sequencing template (i.e., the formed duplex has sufficiently high $T_m$) that the anchor-sequencing template-probe complex will survive stringent washing to remove unbound targets and probes, but they do not overlap with the target site that is complementary to the probe antisense sequence.

In one embodiment, a capture template or target nucleic acid is used as a template for bridge amplification. In such embodiments, two or more different immobilized probes are used. In some cases, single molecule templates are used to generate clusters of nucleic acids on a substrate by bridge amplification. In one embodiment, each of the clusters of nucleic acids contains substantially the same (>95%) type of nucleic acids because they are derived from a single template nucleic acid. These clusters are typically referred to as single molecule clusters. Such substrates with single molecular clusters can be produced using, for example, the method described in Bently et al., Accurate whole human genome sequencing using reversible terminator chemistry, Nature 456, 53-59 (2008), incorporated herein by reference, or using commercially available kit and instrument from, for example, Illumina, Inc. (San Diego, Calif.).

Another method for generating suitable nucleic acids for sequencing is described in Church et al., US Patent Application Publication No. US20090018024 A1, incorporated herein by reference. Additional exemplary methods for generating a suitable template for sequencing include emulsion PCR with DNA capture, with beads that are used to create random arrays (commercially available from, for example, Life Technologies, Inc.) or nanoballs created after rolling circle amplification of constructs that contact target molecules and deposition on patterned arrays (commercial service using the technology is available from, for example, Complete Genomics, Inc.).

The solid substrate can be made of any material to which the molecules can be bound, either directly or indirectly. Examples of suitable solid substrates include flat glass, quartz, silicon wafers, mica, ceramics and organic polymers such as plastics, including polystyrene and polymethacrylate. The surface can be configured to act as an electrode or a thermally conductive substrate (which enhances the hybridization or discrimination process). For example, micro and sub-micro electrodes can be formed on the surface of a suitable substrate using lithographic techniques. Smaller nanoelectrodes can be made by electron beam writing/lithography. Electrodes can also be made using conducting polymers which can pattern a substrate by ink-jet printing devices by soft lithography or be applied homogenously by wet chemistry. $TnO_2$ coated glass substrates are available. Electrodes can be provided at a density such that each immobilized molecule has its own electrode or at a higher density such that groups of molecules or elements are connected to an individual electrode. Alternatively, one electrode may be provided as a layer below the surface of the array which forms a single electrode. The solid substrate may optionally be interfaced with a permeation layer or a buffer layer. It is also possible to use semi-permeable membranes such as nitrocellulose or nylon membranes, which are widely available. The semi-permeable membranes can be mounted on a more robust solid surface such as glass. The surface layer may comprise a sol-gel. The surfaces may optionally be coated with a layer of metal, such as gold, platinum or other transition metal. A particular example of a suitable solid substrate is the commercially available SPR BIACore™ chip (GE Healthcare). Heaton et al., 2001 (PNAS 98:3701-3704) have applied an electrostatic field to an SPR surface and used the electric field to control hybridization.

The solid substrate is generally a material having a rigid or semi-rigid surface. In one embodiment, at least one surface of the substrate is substantially flat, although in some embodiments it may be desirable to physically separate discrete elements with, for example, raised regions or etched trenches. For example, the solid substrate may comprise nanovials—small cavities in a flat surface e.g. 10 µm in diameter and 10 µm deep. Other formats include but are not limited to synthetic or natural beads, membranes or filters, slides including microarray slides, microtiter plates, microcapillaries, and microcentrifuge tubes.

In one embodiment, oligonucleotide capture probes are coated or attached onto beads for capturing the sequencing templates. Hybridization between capture probes and sequencing template polynucleotides can be carried out on beads in columns at a controlled temperature and salt concentration. The hybridization products can be eluted from the beads with moderate pressure.

The use of a solid support with an array of capture oligonucleotides is disclosed in U.S. Pat. No. 6,852,487, which is hereby incorporated by reference.

Loading of nucleic acids onto these substrates can be modulated and/or controlled by the flow and/or electrical forces, including diffusion forces and surface forces exerted by areas of differential charge and/or hydrophobicity. The number of nucleic acids applied to the substrate (i.e., with a loading buffer or other solution) can be adjusted to assure maximal occupancy of the linear features with non-overlapping nucleic acid molecules and thus minimize the number of empty linear features on the substrate. In an exemplary embodiment, at least 50% of the linear features of a substrate are occupied by at least one nucleic acid molecule. In a further embodiment, at least 60%, 70%, 80%, 90%, and 95% of the linear features are occupied by one or more nucleic acids.

Two exemplary approaches of laying probes are disclosed herein below for illustrative purposes. The first approach is in situ oligonucleotide synthesis in which the probes are in known geographic locations in the X-Y coordinate plane. In one embodiment, the oligonucleotide probe is synthesized on the surface. Examples of technologies that allow on-surface oligo synthesis include but are not limited to photolithography and ink jet. In another embodiment, the pre-synthesized oligonucleotide probes are spotted onto the surface. Various microarray protocols, for example, protocol for Agilent inkjet-deposited pre-synthesized oligo arrays are known to one skilled in the art.

Polymers such as nucleic acids or polypeptides can be synthesized in situ using photolithography and other masking techniques whereby molecules are synthesized in a step-wise manner with incorporation of monomers at particular positions being controlled by methods of masking techniques and photolabile reactants. For example, U.S. Pat. No. 5,837,832 describes a method for producing DNA arrays immobilized to silicon substrates based on very large scale integration technology. In particular, U.S. Pat. No. 5,837,832 describes a strategy called "tiling" to synthesize specific sets of probes at spatially-defined locations on a substrate. U.S. Pat. No. 5,837,832 also provides references for earlier techniques that can also be used. Light directed synthesis can also be carried out by using a Digital Light Micromirror chip (Texas Instruments) as described (Singh-Gasson et al., (1999) Nature Biotechnology 17:974-978). Instead of using photo-deprotecting groups which are directly processed by light, conventional deprotecting groups such as dimethoxy trityl can be employed with light directed methods where, for example, a photoacid molecule bearing a chromophore capable of receiving UV radiation is generated in a spatially addressable way which selectively deprotects the DNA monomers (McGall et al PNAS 1996 93: 1355-13560; Gao et al J. Am. Chem Soc. 1998 120: 12698-12699). Electrochemical generation of acid is another methods that can be used in the subject methods of the present invention.

The in situ arrays can have about 1 to 10, 10 to 100, 100 to 1000, or 1,000 to 100,000,000 probes. The in situ arrays can have more than 100,000,000 array probes. In one embodiment, the in situ array carries approximately 200,000,000 probes.

Molecules that can be immobilized in the array include nucleic acids such as DNA and analogues and derivatives thereof, such as PNA. Nucleic acids can be obtained from any source, for example genomic DNA or cDNA or synthesized using known techniques such as step-wise synthesis. Nucleic acids can be single or double stranded. DNA nanostructures or other supramolecular structures can also be immobilized. Other molecules include but are not limited to compounds joined by amide linkages such as peptides, oligopeptides, polypeptides, proteins or complexes containing the same; defined chemical entities, such as organic molecules; conjugated polymers and carbohydrates or combinatorial libraries thereof.

In one embodiment, the biotinylated beads is used to anchor the target sequence and the sequencing as carried out by performing the base incorporation in the bead system.

In another embodiment, a "chip" is a substrate for immobilizing or attached a target. The geometric design of the chip can vary. For example, the chip can be a tube with the usable surface inside. Chips can be in flow cell format to facilitate liquid handling. In one embodiment, the chips are allele specific sequencing chips as disclosed in PCT/US2010/048526, herein is incorporated by reference.

In one embodiment, the chip is a membrane multichip. Multilayered substrate with holes (1 micron to 50 micron) are generated. Target molecules are loaded into the holes with some holes with single molecule target. Targets are amplified within holes. The layers are peeled off. Each layer has some molecules attached to the holes. The layers are substantially similar in terms of molecules (copies of each other). These layers can be directly used or transferred to a suitable sequencing substrate for sequencing.

Other chips can also be used in the present invention, include but are not limited to photo cleavable oligo multichip, multilayer substrates with holes, and nanopriting chip.

In one embodiment, the biotinylated beads is used to anchor the target sequence and the sequencing are carried out by performing the base incorporation in the bead system.

An immobilized or attached target nucleic acid can then be hybridized with a primer (or multiple primers). Polymerase in its suitable buffer is then added to make contact with the immobilized or attached template or target nucleic acid. The buffer may contain a set of nucleotides (1-3 nucleotides of the four possible nucleotides) or the set of nucleotides can be added later to start the reaction. After a suitable amount of time (such as approximately, 5, 10, 15, 20, 25, or 30 to 90 second for native bases), the buffer solution is removed and the immobilized template is washed to remove the nucleotides. Optionally, nucleotide degrading enzymes such as apyrase or alkaline phosphatase are added into the reaction buffer at the end of the reaction and/or in the washing solution to minimize contamination of the next round of extension with nucleotides from the previous extension.

In some embodiments, base extension is performed using a pulse method, such as described herein. In some embodiments, the immobilized template is contacted with a multi-enzyme buffer that contains a polymerase (such as Klenow exo(-) for DNA sequencing), one or several nucleotide degrading enzymes such as apyrase, alkaline phosphatase. Optionally, an inorganic pyrophosphatase is added to degrade pyrophosphate generated by polymerase reaction. Sets of nucleotides are successively added to the reaction buffer at interval of 30-90 seconds (preferably 30 seconds). Nucleotides are utilized by the polymerase for polymerase reaction and at the same time, are degraded by apyrase or alkaline phosphatase.

Template Cluster

For sequencing multiple target polynucleotides (or fragments of a single large polynucleotide target), a large number of different target polynucleotides or its fragments can be immobilized on a substrate. Such a substrate is replicated many times to produce a set of the substrates.

In one embodiment, a plurality of target nucleic acids or templates are immobilized on substrates and each template cluster is originated from a single molecule (see for example, Bentley et al., Nature 456, 53-59, (2008) and its supplement, incorporated herein by reference in its entirety). Because the location of the template cluster are known, a first sequence from the first round of sequencing and second sequence from a second round of sequencing for the same template can be readily determined.

In one embodiment, parallel sequencing is performed. In parallel sequencing, commonly referred to as next generation sequencing, millions or more template (clusters) are sequenced simultaneously often with a single primer. In one embodiment, nucleotide addition is optimized to control primer extension length.

In another embodiment, a fixed sequence of nucleotide addition such as step one: dATP, dCTP, dGTP; step two, dCTP, dGTP, dTTP; step three: dGTP, dTTP, dATP; step four; dTTP, dATP, dCTP; step five: dATP, dCTP, dGTP, and so forth, is used to control the length of the primer extension. Because template sequences vary, the resulting extended primer length varies.

In one embodiment, multiple targets such as 10,000, 100,000, 1 million, 10 million, or 100 million sequences or targets are sequenced simultaneously. Thus, for each substrate, there are a plurality of capture sites with each capture sites have different capture probes that recognize different targets (sequencing templates). If the targets are fragments of a longer sequence, contigs can be assembled to obtain the longer sequence, such as the whole genome sequence. In general, multiple target sequencing is typically done in chip format, but it can be performed in bead format as well.

In one embodiment, the chip comprises random clusters started with single molecules (such as Illumina flow cells). The molecular clones of target molecules can be printed to many substrates to create replicate substrates for sequencing. In one embodiment, the chips are duplicating chips by nylon membrane impression and printing or other methods known in the art.

Sequencing System

Figure 9:
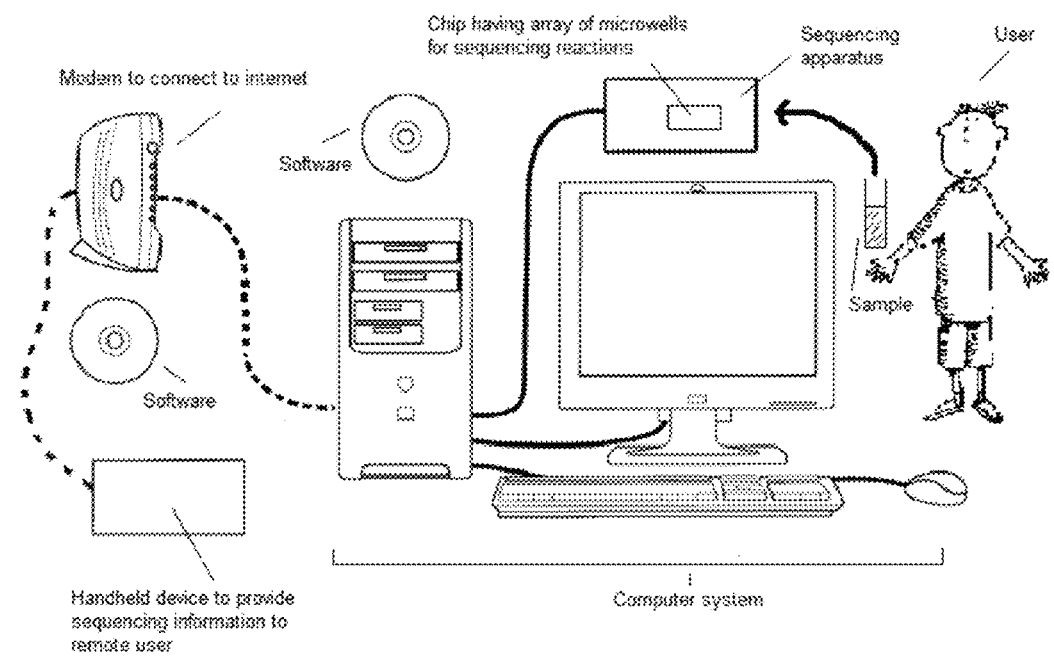
FIG. 9 depicts that nucleic acid sequence information can be obtained, processed, analyzed and/or assembled via a computer system.

In another aspect, the present invention provides a system for sequencing. In some embodiments, one or more methods of sequencing disclosed herein is performed by a system, such as an automated sequencing system instrument controlled by a user (e.g., as schematically depicted in FIG. 9).

In one embodiment, the user controls a computer which may operate various instrumentation, liquid handling equipment or analysis steps of the invention. In one embodiment, a computer controlled collection, handling, or analysis system is used to control, activate, initiate, continue or terminate any step or process of the methods as herein described. In one embodiment, a computer device is used to control, activate, initiate, continue or terminate the handling and/or movement of fluids or reagents into and through the system or device as herein described, the handling or movement of one or more reagents to one or more chambers or plurality of chambers in one or more cartridges, the obtaining or analysis of data, etc. In one embodiment, chips of the sequencing reaction are placed in one or more chambers/flow cells or plurality of chambers/flow cells in one or more cartridges. The chips may comprise substrates which provide sites for the sequencing reactions.

In one embodiment, the computer is any type of computer platform such as a workstation, a personal computer, a server, or any other present or future computer. The computer typically includes known components such as a processor, an operating system, system memory, memory storage devices, and input-output controllers, input-output devices, and display devices. Such display devices include display devices that provides visual information, this information typically may be logically and/or physically organized as an array of pixels. In one embodiment, a graphical user interface (GUI) controller is included that comprises any of a variety of known or future software programs for providing graphical input and output interfaces. In one embodiment, GUI's provide one or more graphical representations to the user, and are enabled to process the user inputs via GUI's using means of selection or input known to those of ordinary skill in the related art.

It will be understood by those of ordinary skill in the relevant art that there are many possible configurations of the components of a computer and that some components that may typically be included in a computer are not described, such as cache memory, a data backup unit, and many other devices. In the present example each execution core may perform as an independent processor that enables parallel execution of multiple threads.

In one embodiment, the processor executes operating system, which is, for example, a WINDOWS™ type operating system (such as WINDOWS™ XP) from the Microsoft Corporation; the Mac OS X operating system from Apple Computer Corp. (such as 7.5 Mac OS X v10.4 "Tiger" or 7.6 Mac OS X v10.5 "Leopard" operating systems); a UNIX™ or Linux-type operating system available from many vendors or what is referred to as an open source; or a combination thereof. The operating system interfaces with firmware and hardware in a well-known manner, and facilitates processor in coordinating and executing the functions of various computer programs that may be written in a variety of programming languages. The operating system, typically in cooperation with the processor, coordinates and executes functions of the other components of computer. The operating system also provides scheduling, input-output control, file and data management, memory management, and communication control and related services, all in accordance with known techniques.

In one embodiment, the system memory is of a variety of known or future memory storage devices. Examples include any commonly available random access memory (RAM), magnetic medium such as a resident hard disk or tape, an optical medium such as a read and write compact disc, or other memory storage device. Memory storage devices may be any of a variety of known or future devices, including a compact disk drive, a tape drive, a removable hard disk drive, USB or flash drive, or a diskette drive. Such types of memory storage devices typically read from, and/or write to, a program storage medium (not shown) such as, respectively, a compact disk, magnetic tape, removable hard disk, USB or flash drive, or floppy diskette.

In one embodiment, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

In one embodiment, input-output controllers include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers of input-output controllers could include controllers for any of a variety of known display devices for presenting information to a user, whether a human or a machine, whether local or remote. In one embodiment, the functional elements of computer communicate with each other via system bus. Some of these communications may be accomplished in alternative embodiments using network or other types of remote communications.

In one embodiment, applications communicate with, and receive instruction or information from, or control one or more elements or processes of one or more servers, one or more workstations, and/or one or more instruments. In one embodiment, a server or computer with an implementation of applications stored thereon are located locally or remotely and communicate with one or more additional servers and/or one or more other computers/workstations or instruments. In one embodiment, applications are capable of data encryption/decryption functionality. For example, it may be desirable to encrypt data, files, information associated with GUI's or other information that may be transferred over network to one or more remote computers or servers for data security and confidentiality purposes.

In one embodiment, applications include instrument control features, where the control functions of individual types or specific instruments such as a temperature controlling device, imaging device, or fluid handling system are organized as plug-in type modules to the applications. In one embodiment, the instrument control features include the control of one or more elements of one or more instruments that, for instance, include elements of a fluid processing instrument, temperature controlling device, or imaging device. In one embodiment, the instrument control features are capable of receiving information from the one or more instruments that include experiment or instrument status, process steps, or other relevant information. In one embodiment, the instrument control features are under the control of an element of the interface of the applications. In one embodiment, a user inputs desired control commands and/or receive the instrument control information via one of GUI's.

In one embodiment, the automated sequencing system is controlled by a first user, conducts sequencing methods described herein, analyzes the raw data as described herein, assembles sequence reads as described herein, and then send the sequencing information to a remote second user at a location different from that of the first user.

Processing of Data and Data Analysis

In one embodiment, identifying target polynucleotide sequence and integrating sequences to assemble genomic information is carried out with a computer. In one embodiment, the present invention encompasses a computer software or algorithm designed to analyze and assemble sequence information obtained via the methods of the present invention.

In terms of sequence read interpretation for the in situ arrays, reads at array features correspond to X-Y coordinates that map to the loci of interest. A "read" typically refers to an observed sequence derived from raw data, such as the order of detected signals corresponding to the cyclical addition of individual nucleotides.

In one embodiment, the reads are checked against the expected reference genome sequence at the 10-bp loci for quality control. A reference sequence enables the use of short read length. Reads that have passed the quality control check are then combined to generate a consensus sequence at each locus. In one example, there are 10 unique probes per locus of interest minus any reads that have failed the quality control checks.

In terms of sequence read interpretation for the "lawn" approach, the reads are at random locations on a surface, e.g. a flow cell. In one embodiment, the reads are checked against the expected subset of reference genome sequence at the loci of interest for quality control. Reads that have passed the quality control check are mapped to the individual locus of interest. Reads corresponding to each locus are then combined to generate a consensus sequence. In one embodiment, there are more than 3,000 reads per 10-bp locus.

Assembly of Sequence Reads

In one embodiment, the present invention provides a method for obtaining the sequence information of the target molecules by assembling the sequence reads from each of the substrates. The sequence reads can be obtained by base extension of a series of polynucleotide with different lengths due to the different base extension of the same capture probe using the same target molecules, such as described above. As such, they represent continued fragments of the target molecule sequence and can be assembled to provide the continue sequence of the target molecule.

A computer program can be used to track the sequence reads obtained from the same capture probes on different substrates for the assembly.

Applications

The methods of the present invention provide several advantages. In one embodiment, the sequencing methods provided herein permit the use of unmodified nucleotide and enzymes, which utilize the natural nucleic acid synthesis chemistry. This not only reduces the cost, but also increases the accuracy because the high-fidelity chemistry generated by the evolution process.

The sequencing method provided by the present invention can be used to sequence DNA/RNA. It can be used to sequence pathogens/microbial genomes to identify species/strains quickly. One advantage of the sequencing method provided by the present invention is that is can accommodate low efficiency sequencing chemistry (reversible terminators, ligations, etc.), thus reduces the time to sequence. In addition, the method can sequence very long fragments (e.g. 100-10000 base pairs or more).

Furthermore, when loci- and allele-specific sequencing templates are used, they are SNP capable, and can carry multiple signal-reporting labels or ligands, providing for a higher level of multiplexing of diverse target sequences.

Thus, the present invention can provide low-cost, high-throughput and accurate methods for sequencing target polynucleotide, with long reads.

The sequencing methods of the present invention can be multiplexed to a very high degree. In one embodiment, samples can comprise pooled genomes of target and control subject populations respectively. Populations can be of any sex, race, gender or age. Populations can also include animal subjects, particularly mammalian subjects such as dog, cat, horse, mouse, rat, etc., screened for veterinary medicine or pharmaceutical drug development purposes.

In another embodiment, the sequencing method provided herein use single molecule counting for accurate analysis of allele frequencies and/or haplotype frequencies. Since more than a single site on each molecule can be probed, haplotype information can be easily determined. In another embodiment, the present methods and systems disclosed herein can be used to obtain haplotype frequencies. Such methods can be applicable to association studies, where genotype frequencies (such as SNP frequencies) are correlated with diseases in a population. The expense of single SNP typing reactions can be prohibitive when each study requires the performance of millions of individual reactions; the present invention permits millions of individual reactions to be performed and analyzed on a single array surface.

In one embodiment, the sequencing methods provided herein are used for identifying high value polymorphisms located in regulatory elements and coding regions for a number of drug metabolizing enzyme and transporter (DMET) genes. In one embodiment, information on the expression of DMET genes provides information on the absorption, distribution, metabolism, and excretion profiles of a drug. In one embodiment, the methods of the present invention provide for information collected on the complex transcriptional responses to various drugs and subsequent prediction of physiological effects is important for the development of effective therapeutics. In one embodiment, the sequencing methods provided herein are used to draw links between gene expression profiles and physiological effects. Physiological effects can include a subjects' likely response to a drug candidate.

A wide variety of diseases can be detected by the process of the present invention. In one embodiment, the sequencing methods provided herein are used for detecting infectious diseases. Infectious diseases can be caused by a pathogen, such as a bacterial, viral, parasitic, or fungal infectious agent. In one embodiment, resistance of various infectious agents to drugs is determined using the methods of the present invention.

In one embodiment, the sequencing methods provided herein are used to sequence pathogens/microbial. In one embodiment, the sequencing methods provided herein are used to identify species/strains. In one embodiment, the sequencing methods provided herein are used to sequence pathogens/microbial and to identify species/strains.

For example, the sequencing method provided herein can be used for detecting one or more microbes. Detection of a microbe can be by sequencing PCR products from a microbe, such as a virus or bacteria. For example, a viral or bacterial PCR product can be hybridized with 5'-3' chips (direct sequencing) or 3'-5' chips (requires additional sequencing primer). In one embodiment, approximately 20-50 bases or longer sequencing is used, to detect a microbe. In one embodiment, about 10-20 chips, wherein a chip density of 10 k can produce approximately 200 k to 500 k base sequence, is used.

In one embodiment, the sequencing methods provided herein are used to detect genetic diseases. In one embodiment, detection is carried out by prenatal or post-natal screening for chromosomal and genetic aberrations or for genetic diseases. Examples of detectable genetic diseases include, but are not limited to, 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

In one embodiment, the sequencing methods provided herein are used to detect a cancer. In one embodiment, detection of a cancer involves detection of one or more cancer markers. Examples of cancer markers include, but are not limited to, oncogenes, tumor suppressor genes, or genes involved in DNA amplification, replication, recombination, or repair. Specific examples include, but are not limited to, BRCA1 gene, p53 gene, APC gene, Her2/Neu amplification, Bcr/Abl, K-ras gene, and human papillomavirus Types 16 and 18. The sequencing methods provided herein can be used to identify amplifications, large deletions as well as point mutations and small deletions/insertions or other mutations of genes in the following human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

For example, to screen for a cancer marker, the genomic DNA from subject can be prepared as a sequencing template and can be allowed to bind a capture probe fixed to a substrate. In this example there can be multiple substrates each with the same capture probe wherein each substrate can then be exposed to an identical version of the sequencing template. After removal of any unbound sequencing template, the arrays, or chips, are then subjected to incremental base extension. The capture probes can serve as a primer and specifically bind to a region of the sequencing template near a location that can be use for detecting a relevant distinction indicating a disease. In the case of cancer and screening Bcr/Abl, the capture probes can bind in close proximity to the expected translocation site. Incremental extensions of the bases can reveal whether or not the sequencing template contains DNA from only one gene in the region of interest or that from a translocated gene region. After reading the results from step-wise hybridization events across the multiple chips, and processing the raw data, once can then determine if a subject's DNA has a Bcr/Abl translocation, and therefore detect the presence of a genetic sequence indicative of cancer.

In one embodiment, the sequencing methods of the present invention are used for environmental monitoring. Environmental monitoring includes but is not limited to detection, identification, and monitoring of pathogenic and indigenous microorganisms in natural and engineered ecosystems and microcosms such as in municipal waste water purification systems and water reservoirs or in polluted areas undergoing bioremediation. In one embodiment, the methods of the present invention are used to detect plasmids containing genes that can metabolize xenobiotics, to monitor specific target microorganisms in population dynamic studies, or either to detect, identify, or monitor genetically modified microorganisms in the environment and in industrial plants.

In one embodiment, the sequencing methods provided herein are used in a variety of forensic areas. Examples of forensic areas include, but are not limited to, human identification for military personnel and criminal investigation, paternity testing and family relation analysis, HLA compatibility typing, and screening blood, sperm, and transplantation organs for contamination.

In the food and feed industry, the present invention has a wide variety of applications. In one embodiment, the sequencing methods provided herein are used for identification and characterization of production organisms. Examples of production organisms include, but are not limited to, yeast for production of beer, wine, cheese, yogurt, and bread. In one embodiment, the methods of the present invention are used for quality control and certification of products and processes (e.g., livestock, pasteurization, and meat processing) for contaminants. In one embodiment, the sequencing methods provided herein are used for characterization of plants, bulbs, and seeds for breeding purposes, identification of the presence of plant-specific pathogens, and detection and identification of veterinary infections.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the present invention described herein may be employed in practicing the present invention. It is intended that the following claims define the scope of the present invention and that methods and structures within the scope of these claims and their equivalents be covered thereby.

EXAMPLES

Example 1

Dark Base (Native Nucleotide) Extension

A sequencing template was immobilized on streptavidin coated beads via its 5' biotin and was hybridized with a sequencing primer by incubating at 70° C. for 3 min., 55° C. for 15 min and 25° C. for 5 min. In a 50 µl reaction, 8U Klenow exo(−), 65 mU of apyrase, 10 mU of inorganic pyrophosphatase, and 5 µg of single strand binding protein (SSB) were added. The extension reactions were carried out at room temperature. At one minute interval, successive sets of nucleotides, 6.7 µM final concentration each, were added to the reaction buffer with mixing. Three dark bases were added at each step as depicted in FIG. 1. After 5 step dark base additions as depicted in FIG. 1, the beads were washed and a fresh reaction buffer with enzymes and SSB was added to the beads. After some nucleotide addition steps, for example, after Steps 9, 10, and 12 as depicted in FIG. 1, in which the results are depicted in FIG. 3, an aliquot of beads was taken out and treated with NaOH to release the extended primer. The extension products were examined using denaturing polyacrymide gel and the signals were analyzed using ImageJ (available from the National Institute of Heath). A general schematic of the protocol is depicted in FIG. 2.

The results of the extension products are depicted in FIG. 3. The largest band is the expected extension product. The primary product of the extension was as expected in length.

Figure 4:
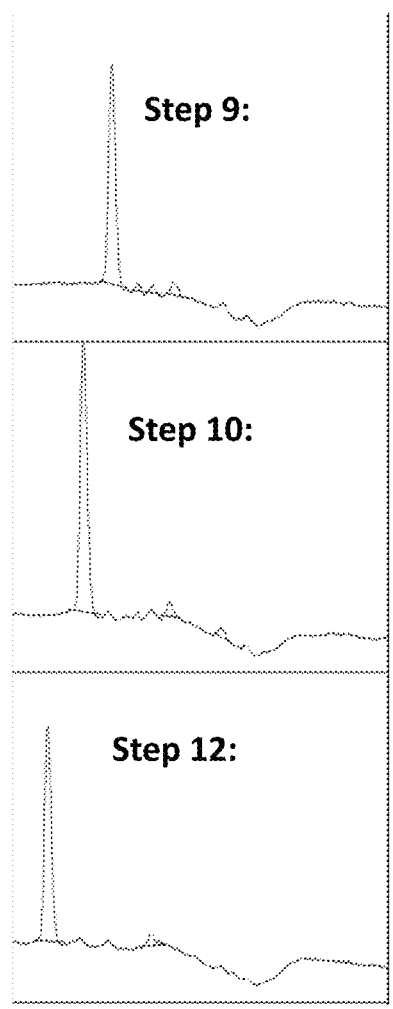
FIG. 4 depicts results of an exemplary embodiment of the present invention, in which 12 steps of 3-base extension resulted in a 124 bp product (extension plus primer), wherein the template was a PCR product.

Few smaller bands were detected, which may be products of incomplete incorporation and represented small portion of the reaction products. The Step 9 extension product of 85 base pairs (bp), which corresponds to the extension of 63 bp to the 22 bp primer, the Step 10 extension product of 98 bp, which corresponds to the extension of 76 bp to the 22 bp primer, and the Step 12 extension product of 124 bp, which corresponds to the extension of 102 bp to the 22 bp primer, are depicted in FIG. 4.

Example 2

Dark Base (Native Nucleotide) Extension with PCR Product as Template

A PCR product was used as a template in this Example. The PCR template was immobilized on streptavidin coated beads via its 5' biotin and was hybridized with a sequencing primer by incubating at 70° C. for 3 min., 55° C. for 15 min and 25° C. for 5 min. In a 50 μl reaction, 8U Klenow exo(−), 65 mU of apyrase, 10 mU of inorganic pyrophosphatase, and 5 μg of single strand binding protein (SSB) were added. The extension reactions were carried out at room temperature. At one minute interval, successive sets of nucleotides, 6.7 μM final concentration each, were added to the reaction buffer with mixing. Three dark bases were added at each step as depicted in FIG. 1.

The results of the extension products are depicted in FIG. 4. The largest band is the extension product. The primary product of the extension was as expected in length. Few smaller bands were detected, which may be products of incomplete incorporation and represented small portion of the reaction products.

The Step 9 extension product of 85 base pairs (bp), which corresponds to the extension of 63 bp to the 22 bp primer, the Step 10 extension product of 76 bp to the 22 bp primer, and the Step 12 extension product of 124 bp, which corresponds to the extension of 102 bp to the 22 bp primer, are depicted in FIG. 4.

Example 3

Massive Parallel Sequencing Following Dark Base Extension

Massive parallel sequencing following dark base extension was demonstrated using a sequencing flow cell with 8 lanes (commercially available from Illumina, San Diego, Calif.). Sequencing libraries prepared from genomic samples (including samples enriched for exon regions) were prepared and sequenced for 100 bases according to standard protocols using an Illumina HiScanSQ sequencer.

All flow cell lanes were then stripped with 0.1N NaOH to remove sequencing extension products that are labeled with fluorescent signals. The resulting flow cell lanes were washed with SSC washing solution. A sequencing primer (P1) was hybridized with sequencing templates still in the flow cell lanes for 30 minutes at 60° C. The flow cell lanes/channels were then washed with SSC.

For Lane 1, pre-incubation buffer with Klenow, NEB2, pyrophosphatase was loaded and wait for 1 minute. A dark base triplet solution with 13.4 uM each of dTTP, dGTP, and dCTP in buffer was load for one minute then removed. An apyrase wash solution (1 mU/μl) was loaded into the lane and removed after three minutes. Another cycle of dark base extension was then employed. The sequence of dark base extension in terms of missing nucleotides was A, T, G, C, A, T, G, C, A, and T. A total of ten dark base extension steps were used with last missing nucleotide being dTTP.

For Lane 3, pre-incubation buffer with Klenow, NEB2, pyrophosphatase and apyrase (1 mU/μl) was loaded and wait for 1 minute. A dark base triplet solution is spiked into the pre-incubation solution with 13.4 uM each of dTTP, dGTP, and dCTP. The mixed solution was loaded into the flow cell lane for one minute. Another cycle of dark base addition/extension was then employed. The sequence of dark base extension in terms of missing nucleotides was A, T, G, and C. A total of four dark base extension steps were used with last missing nucleotide being dCTP.

After dark base extension, the flow cell was then loaded to an Illumina HiScanSQ sequencer to sequence 25 bases (second sequencing). After the second sequencing, the flow cell lanes were striped again with 0.1 N NaOH and the striped nucleic acids were analyzed using a denaturing gel.

Lane 1 generated about 278 million base reads with about 11 million clusters passed filter. Lane 3 generated about 653 million base reads with about 25.6 million clusters passed filter.

Figure 5:
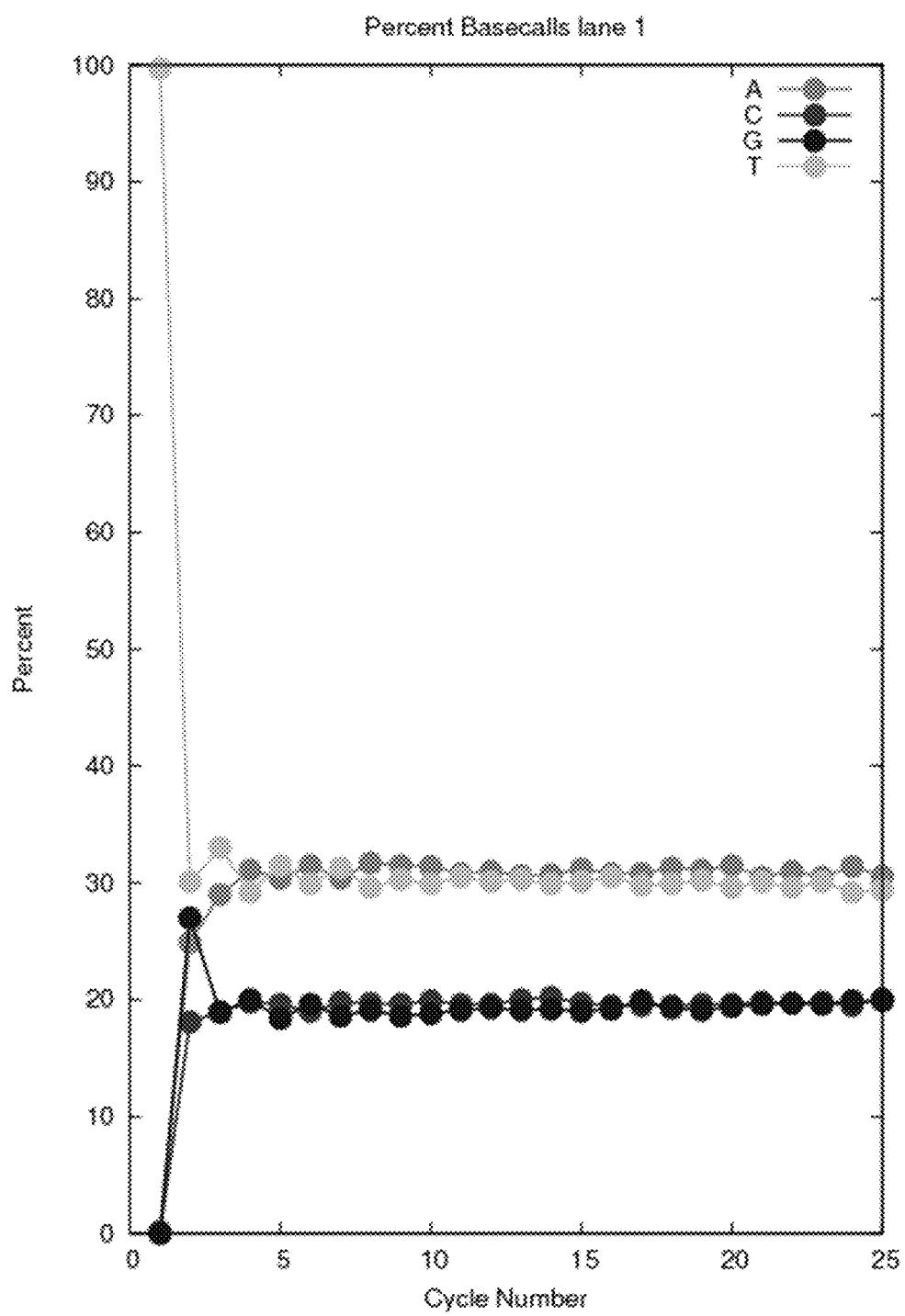
FIG. 5 depicts the percent base calls per sequencing step for lane 1 of an exemplary embodiment of the present invention, where the last step of the dark base extension was a missing T step, and as expected, 100% of the first sequencing base was "T".

FIG. 5 shows the percent base calls per sequencing step for Lane 1. As expected, 100% of the first base was called "T" as the last step of the dark base extension was a "missing T" step, as it is expected that the first base addition in the sequencer after the first base should be "T".

Figure 6:
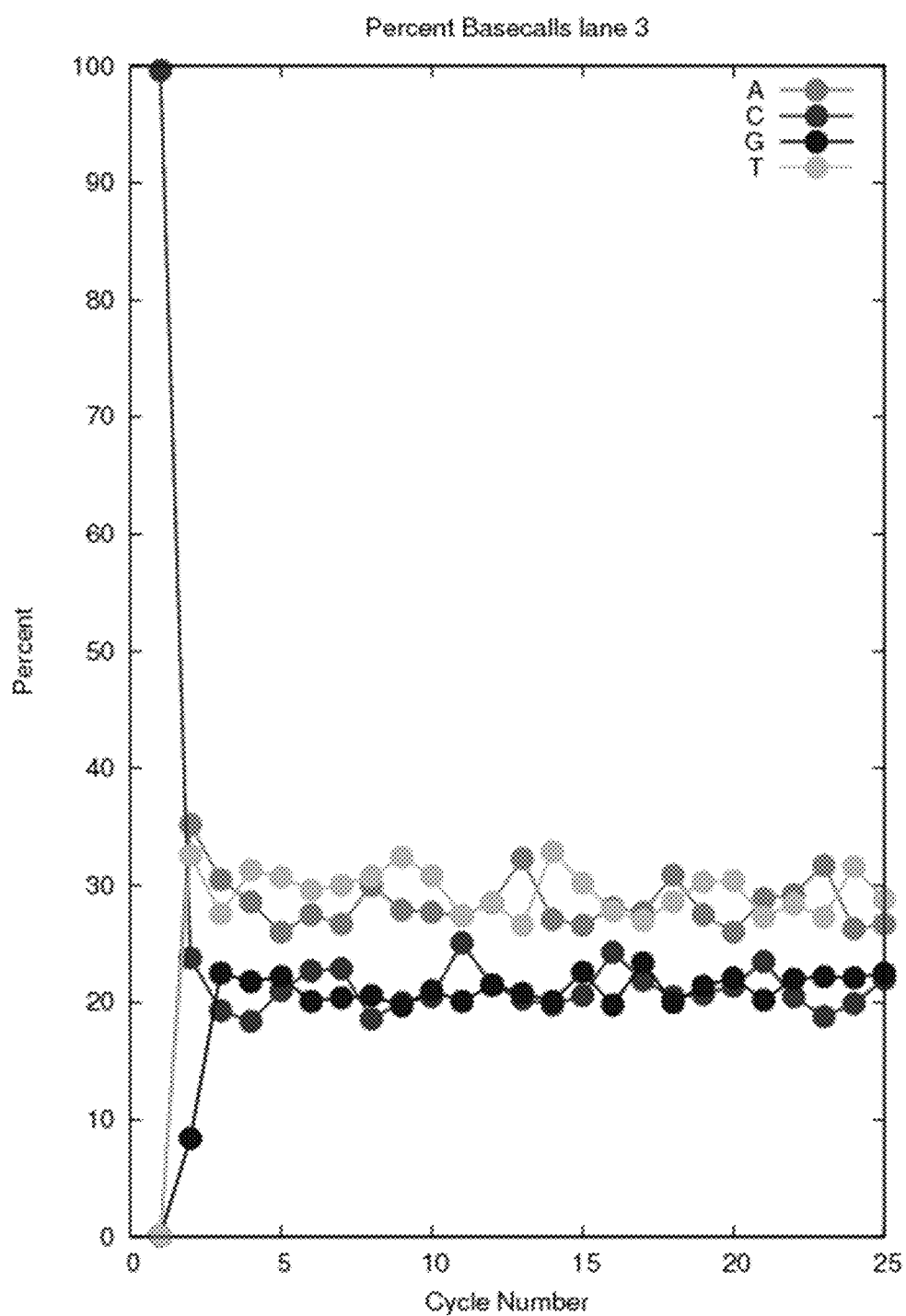
FIG. 6 depicts the percent base calls per sequencing step for lane 3 of an exemplary embodiment of the present invention, where the last step of the dark base extension was a missing C step, and as expected, 100% of the first sequencing base was "C".

FIG. 6 shows the percent base calls per sequencing step for Lane 3. Also as expected, 100% of the first base called was "C."

The sequences from the seconding sequencing were matched with the sequences from the first sequencing as the templates were the same. Because there were alignment changes between the first and second sequencings (flow cell was removed from the sequencer for dark base extension), a search algorithm was used to match the sequences with a range of 150 units of x, y coordinates from the Illumina qseq files. One million passed filter sequences from lane one, second sequencing (25 bases long) were checked and 71.3% of the sequences matched part of the sequences from seconding sequencing (100 bases long). Similarly, one million passed filter sequences from lane three, second sequencing (25 base long) were checked and 76.56% of the sequences matched part of the sequences from seconding sequencing (100 bases long).

Figure 7:
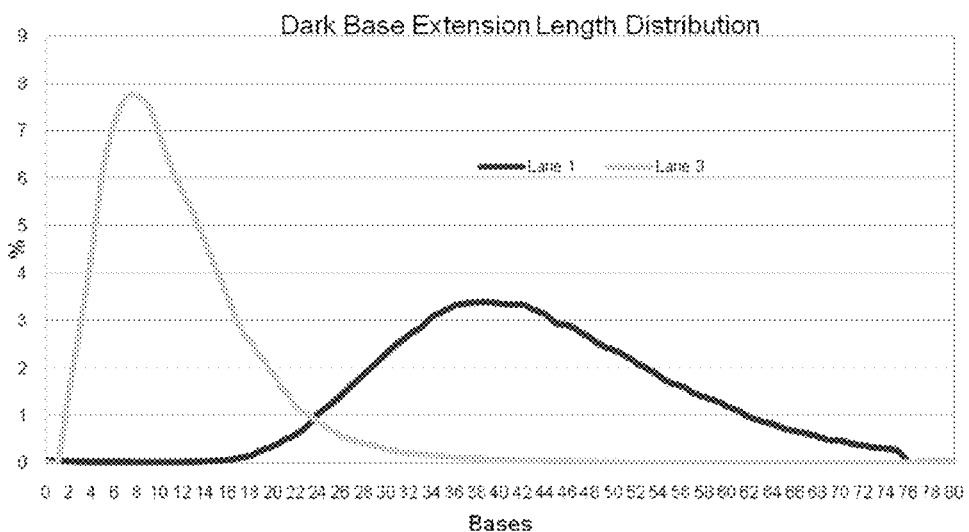
FIG. 7 depicts the distribution of dark base extensions in lane 1 (10 steps) and lane 3 (4 steps).

The sequence match positions were also analyzed. FIG. 7 shows that the distribution of dark base extensions in Lane 1 (10 steps) and Lane 3 (4 steps). These distributions agree with the expected distribution. Both the high exact sequence match and the correct distribution indicate that the sequence after dark extension worked reasonably well.

When 8.8 million sequences from Lane 1 were checked to examine whether the actual dark extension match with expected according to the sequences from sequence 1, 98.2% of the dark base extension was expected. Among the 8.8 million sequences, 8.7 million sequences matched with the 10 steps (ATGC cycle) dark base extension. An additional 5,673 sequences from second sequencing did not have first base calls. Assuming that the first base was "T" as expected for these sequences, they matched with the 10 steps dark base extension.

Example 4

Massively Parallel Sequencing Following Controlled Extension

Massively parallel sequencing following controlled extension was again demonstrated using an Illumina HiScanSQ sequencer. Eight genomic samples enriched for exon regions were used to prepare Illumina pair end sequencing library and sequenced for 75 bases per each end (2×75 bases) according to standard protocol using Agilent and Illumina reagents and protocols. After the second end sequencing (read 2), lanes 1-6 and 8 were used for controlled extension using a cBot cluster generation system (Illumina) customer programmed by Centrillion Biosciences, Inc. to perform controlled extension with custom assembled reagent kit.

The cBot cluster generation system was reprogrammed to utilize a custom edited protocol to deliver nucleotide combinations at specified time interval and other reagents. After all lanes were stripped with 0.1N NaOH (120 µl) to remove sequencing extension products, an Illumina sequencing primer (SP2, 95 µL) was introduced into all lanes in order to hybridize to clusters of ssDNA template on the surface of the flow cell Hybridization was performed for 15 min at 60° C., followed by slow cooling to 20° C. at a rate of 3° C./min.

Controlled extension was accomplished by repeated introduction of unlabeled native nucleotide triplets (85 µL for 1 minute), followed by apyrase containing washing solution (120 µL for 2 minutes).

Finally, a wash solution of NEB2 (120 µL, 1×) was pumped through the flow cell before proceeding to the following dark base extension step. For example, Lane 4—(10 steps), nucleotide combinations were:—missing A, C, G, T, A, C, G, T, A, C Lane 5—(16 steps)—missing A, C, G, T, A, C, G, T, A, C, A, C, G, T, A, C Lane 6—(20 steps)—missing A, C, G, T, A, C, G, T, A, C, A, C, G, T, A, C, G, T, A, C. Lane 7—(0 steps)—control, sequencing primer only (no dark base extension).

After dark base extension, the flow cell was then loaded to an Illumina HiScanSQ sequencer to sequence 75 bases (second sequencing).

Lane 4 generated about 1,927 million base reads with about 25.7 million clusters passed filter. Lane 5 generated about 1,324 million base reads with about 17.6 million clusters passed filter. Lane 6 generated about 884 million base reads with about 11.8 million clusters passed filter.

The sequences from the second sequencing were matched with the sequences from the second read of the first sequencing. Because the second sequencing was extended longer than the second read of the first sequencing, the sequences from the second sequencing may or may not overlap with the sequences from the second read of the first sequencing from the same cluster. The sequences from both sequencing were mapped to human genome, and a search algorithm was used to compare the mapping position on human chromosome to determine if two sequences were from the same cluster based on their mapping positions. Because there were cluster alignment changes between the first and second sequencings (flow cell was removed from the sequencer for dark base extension), the search algorithm considered to match the sequences with a range of 600 units of x, y coordinates from the Illumina qseq files.

One million passed filter sequences from lane 4, second sequencing (75 bases long) were checked and 80.4% of the sequences mapped to the positions next to where the sequences from first sequencing (75 bases long) were mapped. Similarly, one million passed filter sequences from lane 5, second sequencing (75 base long) were checked and 81.8% of the sequences mapped to the positions next to where the sequences from first sequencing (75 bases long) were mapped. Similarly, one million passed filter sequences from lane 6, second sequencing (75 base long) were checked and 82% of the sequences mapped to the positions next to where the sequences from first sequencing (75 bases long) were mapped.

Figure 8:
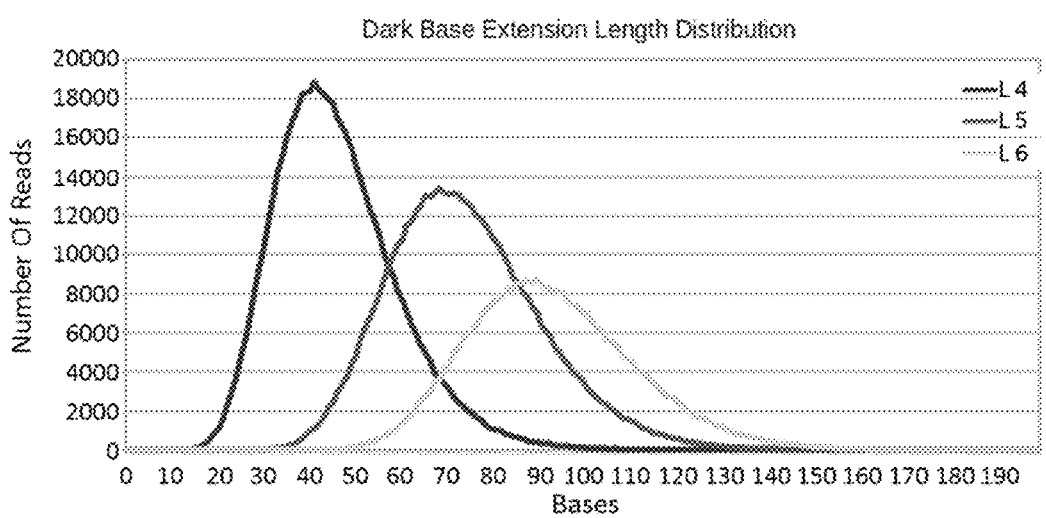
FIG. 8 depicts the distribution of dark base extensions in lane 4 (10 steps), lane 5 (16 steps) and lane 6 (20 steps) in another exemplary embodiment of the present invention.

The sequence match positions were also analyzed. FIG. 8 shows that the distribution of dark base extensions in Lane 4 (10 steps), Lane 5 (16 steps) and Lane 6 (20 steps). These distributions agree with the expected distribution. Both the high sequence mapping position match and the correct distribution indicate that the sequence after dark extension worked reasonably well.

---

What is claimed is:

1. A method for sequencing a target nucleic acid, comprising:
   (a) sequencing one or more bases of a target nucleic acid by extending a first sequencing primer hybridized to said target nucleic acid to generate a first primer extension product, thereby obtaining a first sequence read;
   (b) releasing said first primer extension product from said target nucleic acid;
   (c) hybridizing a second sequencing primer to said target nucleic acid;
   (d) generating a second primer extension product by extending said second sequencing primer through limited extension without the use of labeled nucleotides;
   (e) sequencing one or more bases of said target nucleic acid by further extending said second primer extension product to generate a third primer extension product, thereby obtaining a second sequence read; and
   (f) determining a sequence of said target nucleic acid by assembling said first sequence read and said second sequence read.

2. The method of claim 1, wherein said first sequencing primer and said second sequencing primer are the same.

3. The method of claim 1, wherein said first sequencing primer and said second sequencing primer are different.

4. The method of claim 1, wherein said limited extension is carried out by pulse extension.

5. The method of claim 4, wherein said pulse extension is carried out by allowing the extending reaction to last 30 to 60 seconds.

6. The method of claim 1, wherein said limited extension is carried out by using a nucleic acid polymerase and one or more sets of nucleotides, wherein each set comprises not more than three different nucleotides.

7. The method of claim 6, wherein said extending is with more than one set of nucleotides.

8. The method of claim 7, wherein said set of nucleotides comprises three different nucleotides.

9. The method of claim 6, wherein prior to a subsequent addition of a set of nucleotides a washing step is performed.

10. The method of claim 6, wherein prior to a subsequent addition of a set of nucleotides a nucleotide degradation step is performed.

11. The method of claim 1, further comprising repeating steps (b) to (e) by releasing the primer extension product generated in step (e), thereby obtaining one or more additional sequence reads.

12. The method of claim 11, wherein the sequence of said target nucleic acid is determined by assembling said first, second, and at least one of the one or more additional sequence reads.

13. The method of claim 1, wherein said sequencing in (a) is by extending the first sequencing primer using a labeled reversible terminator or said sequencing in (e) is by further extending the second primer extension product using a labeled reversible terminator.

14. The method of claim 1, wherein said target nucleic acid is attached to a substrate.

15. The method of claim 14, wherein said substrate is a flat surface or bead.

16. The method of claim 14, wherein said substrate is a flow cell.

17. The method of claim 14, wherein said substrate comprises glass.

18. The method of claim 14, wherein said target nucleic acid is attached to said substrate via a capture probe.

19. The method of claim 1, further comprising analyzing said sequencing results to provide a diagnosis, prognosis, or theranosis for a subject.

20. The method of claim 1, comprising sequencing a plurality of target nucleic acids.

21. A method for sequencing a target nucleic acid, comprising:
   (a) sequencing one or more bases of a target nucleic acid by extending a first sequencing primer hybridized to said target nucleic acid to generate a first primer extension product, thereby obtaining a first sequence read;
   (b) releasing said first primer extension product from said target nucleic acid;
   (c) hybridizing a second sequencing primer to said target nucleic acid;
   (d) generating a second primer extension product by extending said second sequencing primer by a first number of nucleotides through limited extension without the use of labeled nucleotides;
   (e) sequencing one or more bases of said target nucleic acid by further extending said second primer extension product to generate a third primer extension product, thereby obtaining a second sequence read;
   (f) releasing said third primer extension product from said target nucleic acid;
   (g) hybridizing a third sequencing primer to said target nucleic acid;
   (h) generating a fourth primer extension product by extending said third sequencing primer by a second number of nucleotides through limited extension without the use of labeled nucleotides;
   (i) sequencing one or more bases of said target nucleic acid by further extending said fourth primer extension product to generate a fifth primer extension product, thereby obtaining a third sequence read; and
   (j) determining a sequence of said target nucleic acid by assembling said first sequence read, said second sequence read, and said third sequence read, wherein said first number of nucleotides is different from said second number of nucleotides.

22. The method of claim 21, wherein said first number of nucleotides and said second number of nucleotides are different by at least 10 nucleotides.

23. The method of claim 1 or claim 21, wherein said sequencing in (a) and said sequencing in (e) comprise sequencing by synthesis.

24. The method of claim 21, wherein said target nucleic acid is immobilized on a solid support.

25. The method of claim 1 or claim 21, wherein said first sequence read and said second sequence read are each at least 5 bases long.

26. The method of claim 1 or claim 21, wherein said first sequence read and said second sequence read are each at least 10 bases long.

* * * * *